US007482508B2

(12) United States Patent
Burn et al.

(10) Patent No.: US 7,482,508 B2
(45) Date of Patent: Jan. 27, 2009

(54) METHODS AND MEANS FOR MODULATING CELLULOSE BIOSYNTHESIS IN FIBER PRODUCING PLANTS

(75) Inventors: Joanne Elizabeth Burn, Murrumbateman (AU); Richard Edward Williamson, Murrumbateman (AU)

(73) Assignee: Australian National University, Canberra (AU)

( * ) Notice: Subject to any disclaimer, the term of this patent is extended or adjusted under 35 U.S.C. 154(b) by 418 days.

(21) Appl. No.: 10/733,407

(22) Filed: Dec. 12, 2003

(65) Prior Publication Data

US 2004/0268433 A1 Dec. 30, 2004

Related U.S. Application Data

(60) Provisional application No. 60/432,674, filed on Dec. 12, 2002.

(51) Int. Cl.

| | |
|---|---|
| ***C12N 15/29*** | (2006.01) |
| ***C12N 5/04*** | (2006.01) |
| ***C12N 5/10*** | (2006.01) |
| ***A01H 3/00*** | (2006.01) |
| ***A01H 5/00*** | (2006.01) |

(52) U.S. Cl. ...................... 800/278; 435/415; 435/416; 435/417; 435/419; 435/468; 536/23.2; 536/23.6; 800/284; 800/298; 530/350; 530/370

(58) Field of Classification Search ................ 435/69.1; 800/298

See application file for complete search history.

(56) References Cited

U.S. PATENT DOCUMENTS 6,316,698 B1 11/2001 Allen et al.

FOREIGN PATENT DOCUMENTS

| | | | |
|---|---|---|---|
| JP | 2000-41685 | A | 2/2000 |
| WO | 97/24448 | A1 | 7/1997 |
| WO | 98/50568 | A1 | 11/1998 |
| WO | WO 03/098186 | | 11/2003 |

OTHER PUBLICATIONS

Zuo et al., "Korrigan, an *Arabidopsis* Endo-1,4-β-Glucanase, Localizes to the Cell Plate by Polarized Targeting and Is Essential for Cytokinesis," *The Plant Cell*, Jul. 2000, vol. 12, 1137-1152, American Society of Plant Physiologists.

Peng et al., "Fractionation of carbohydrates in *Arabidopsis* root cell walls shows that three radial swelling loci are specifically involved in cellulose production," *Planta*, 2000, vol. 211, 406-414, Springer-Verlag.

Monroe et al., Structure, Properties, and Tissue Localization of Apoplastic α-Glucosidase in Crucifers, *Plant Physiology*, Feb. 1999, vol. 199, 385-397, American Society of Plant Physiologists.

Lane et al., "Temperature-Sensitive Alleles of RSW2 Link the Korrigan Endo-1,4-β-Glucanase to Cellulose Synthesis and Cytokinesis in *Arabidopsis," Plant Physiologyl*, May 2001, vol. 126 278-288, *American Society of Plant Physiologists*.

His et al., "Altered pectin composition in primary cell walls of *Korrigan*, a dwarf mutant of *Arabidopsis* deficient in a membrane-bound endo-1,4-β-glucanase," *Planta*, 2001, vol. 212, 348-358, Springer-Verlag.

Nicol et al. "A plasma membrane-bound putative endo-1,4-β-D-gluanase is required for normal wall assembly as cell elongation in *Arabidopsis*" The EMBO Journal, 17:5563-76, 1998.

*Primary Examiner*—Anne Marie Grunberg
*Assistant Examiner*—Brendan O. Baggot
(74) *Attorney, Agent, or Firm*—Buchanan Ingersoll & Rooney PC

(57) ABSTRACT

The present invention provides novel genes involved in cellulose biosynthesis and methods using such genes to modulate cellulose biosynthesis in fiber-producing plants such as cotton. The invention also provides methods for identifying and isolating alleles of these genes in a population of fiber-producing plants that correlate with the quality of the produced fibers.

14 Claims, 8 Drawing Sheets

```
Arabidopsis   1  ----------MRS--LLFVLSLICFCSQTALSWKKEEFRSCDQTPFCKRAR---SRTPGA--CSLIVGDVSITDGDLVAKLLPKAPNQGDGDQIKPLILSLSVYKDGIVRLKIDEDHSLN
potato        1  ----------MRAPLLLYPLLLLLFVTSAYSWKKEEFRNCDQTPFCKRAR---SRKPGS--CNLRVADVSISDGDLIAKLVPKEENPESEQPNKPLVLTLSVYQDGVMRVKIDEDQNLN
mouse         1  MAAIAAVAARRRRSWLSLVLAYLGVCLGITLAVDRSNFKTCDESSFCKRQR---SIRPGLSPYRALLDTLQLGPDALTVHLIHEVTK-------VLLVLELQGLQKNMTRIRIDE---LE
yeast         1  -------MRYHGICWFIFQAAIIFAIFGSCQGAFRHDFKTAEQDGFARRNRDLAKFQKENLNWNGLFQLNSISYNSGVVSGVFEQQS-ENGENQHLFPFSISFLKNDVVRFQMDE-----

Arabidopsis 104  PPKKRFQVPDVVVSEFEEKKIWLQKVATE--TISGDTSPSSVVYVSDGYEAVVRHDP---FEVYVR-------------------------------------------EKSGDRRRVVS
potato      106  PPKKRFEVPEVIEEDFLNTKLWLTRVKEE--QIDGVSSFSSVFYLSDGYEGVLRHDP---FEVFAR-------------------------------------------E-SGSGKRVLS
mouse       108  PRRPRYRVPDVLVADPPTARLSVSGRDDNSVELTVAEGPYKIILTAQPFRLDLLEDRSLLLSVNARGLMAFEHQRAPRVPFSDKVSLALGSVWDKIKNLFSRQESKDPAEGNGAQPEATP
yeast       108  --KSRLEGTVEYEKNILTKRRFDASTELGFNERAEVYGKDAHLLEQTSTSLTIRYGSHGRFTVIVTFS-------------------------------------PFKVEFQRDGEPQVV

Arabidopsis 176  LNSHGLFDFEQLG-------RKTEGDNWEEKFRTHTDSRPSGPQSISFDVSFYDSSFVYGIPEHATSFALKPTKGPGVEE-SEPYRLFNLDVFEYDHESPFGLYGSIPFMVSHGKSGKTS
potato      177  INSNGLFDFEQLR-------EKKEGDDWEEKFRSHTDTRPYGPQSISFDVSFYGADFVYGIPEHATSFALKPTKGPNVEEYSEPYRLFNLDVFEYLHESPFGLYGSIPFMISHGKARGSS
mouse       228  GDGDKPEETQEKA-------EKDEPGAWEETFKTHSDSKPYGPTSVGLDFSLPGMEHVYGIPEHADSLRLKVTEG------GEPYRLYNLDVFQYELNNPMALYGSVPVLLAHSFHR-DL
yeast       189  LNERHLLNMEYYRPKSSRTPEQEANGMWDETFDNFHDSKPKGPESVGLDIKFVDYGNVYGVPEHTSSLSLKETNNSDAG-YTEPYRLYNVDLFEYEVDSPMSQYGAIPFMQAHKPNS-DV

Arabidopsis 288  GFFWLNAAEMQIDVLANGWDAESG------ISLPSSHSRIDTFWMSEAGIVDTFFFVGPEPKDVVKQYASVTGTSAMPQLFATGYHQCRWNYKDEEDVAQVDSKFDEHDIPYDVLWLDIE
potato      290  GFFWLNAAEMQIDVLGSGWNSDES----SKIMLPSDKHRIDTLWMSESGVVDTFFFIGPGPKDVVRQYTSVTGRPSMPQLFATAYHQCRWNYRDEEDVYNVDSKFDEHDIPYDVLWLDIE
mouse       334  GIFWLNAAETWVDISSNTAGKTLFGKMLDYLQGSGETPQTDIRWMSESGIIDVFLMLGPSVFDVFRQYASLTGTQALPPLFSLGYHQSRWNYRDEADVLEVDQGFDDHNMPCDVIWLDIE
yeast       307  AVFWSNAAATWIDVEKESGP-------------SPHSQSTSTHWYSESGTLDLFIFLGPKASDVYESYSALVGRPLLPPLFSIGYHQCRWNYVSEEDVLNVDAKFDEVDMPYDTIWLDIE
                                                                                                                        *
                                                                                                          Ly-WNDMNEPSvF
Arabidopsis 402  HTDGKRYFTWDSVLFPHPEEMQKKLAAKGRKMVTIVDPHIKRDDSYFLHKEATQMGYYVKDSSGKD-FDGWCWPGSSSYIDMLSPEIRKWWGGRFSYKNYVGSTPSLYTWNDMNEPSVFN
potato      406  HTDGKKYFTWDRVLFPNPEEMQKKLAAKGRHMVTIVDPHIKRDESYHIPKEALEKGYYVKDATGKD-YDGWCWPGSSSYTDLLNPEIKSWWSDKFSLDSYVGSTKYLYIWNDMNEPSVFN
mouse       454  HADGKRYFTWDPTRFPQPLNMLEHLASKRRKLVAIVDPHIKVDSGYRVHEELRNHGLYVKTRDGSD-YEGWCWPGSASYPDFTNPRMRAWWSNMFSFDNYEGSAPNLYVWNDMNEPSVFN
yeast       414  YASKRRYFTWDKATFPNPKAMLEKLDSKSRKLIVILDPHIKNDPNYFVSKELIDYNYAVKDKSGVDNYNADCWPGNSVWVDFFNPEAQAWWGSLYEFDRFE-SDKNLWIWNDMNEPSVFR
                                                                                                             *
                                                                                   *                 GADvGGPf.nP.pELIVRWYQ.Gay.
Arabidopsis 521  GPEVTMPRDALHVGGVEHREVHNAYGYYFHMATSDGLVMREEGKDRPFVLSRAIFPGTQRYGAIWTGDNTAEWEHLRVSIPMILTLGLTGITFSGADIGGFFGNPEPELLVRWYQVGAYY
potato      525  GPEVTMPRDALHHGGVEHRELHNSYGYYFHMGTSDGLLKRGDGKDRPFVLARAFFAGSQRYGAIWTGDNTAEWEHLRVSVPMVLTLSISGIVFSGADVGGFFGNPDTELLVRWYQVGAYY
mouse       573  GPEVTMLKDAVHYGGWEHRDIHNIYGLYVHMATADGLIQRSGGIERPFVLSRAFFSGSQRFGAVWTGDNTAEWDHLKISIPMCLSLALVGLSFCGADVGGFFKNPEPELLVRWYQMGAYQ
yeast       533  GPETSMHRDAIHYGGWEHRDIHNIYGHKCINGTYNGLIKRGEGAVRPFILTRSFFAGTSALAANWIGDTMTTWEHLRGSIPTVLTNGISGMAFSGADVAGFFGNPDAELFVRWYETAIFY

                 PFFR.HA
Arabidopsis 641  PFFRGHAHHDTKRREPWLFGERNTELMRDAIHTRYTLLPYFYTLFREANVTGVPVVRPLWMEFPQDEATFSNDEAFMVG-SGLLVQGVYTKGTTQASVYLPG-KESWYDLRNGKTYVGGK
potato      645  PFFRGHAHHDTKRREPWLFGERNTQLMREAIHVRYMYLPYFYTLFREANSSGTPVARPLWMEFPGDEKSFSNDEAFMVG-NGLLVQGVYTEKPKHVSVYLPG-EESWYDLRSASAYNGGH
mouse       693  PFFRAHAHLDTGRREPWLLASQYQDAIRDALFQRYSLLPFWYTLFYQAHKEGFPVMRPLWVQYPEDMSTFSIEDQFMLG-DALLIHPVSDAGAHGVQVYLPGQEEVWYDIQSYQKHHGPQ
yeast       653  PFFRAHAHIDTKRREPWLYGEPYTSLVRELLRIRYRLLPTWYTAFYNSHTHGFPILYPQFLMHPEDEEGFAIDDQFYVGDSGLLVKPVTHPSIDKITIYLAD-DEVYFDLHDHTEYAGKG

Arabidopsis 759  THKMDAPEESIPAFQKAGTIIPRKDRFRRSSSQMDNDPYTLVVALNSS-QEAEGELYIDDGKSFEFR-RGSYIHRRFVFSKGVLTSTN------LAPPEARLSSQCLIDRIILLGHSSGP
potato      763  THKYEVSEDSIPSFQRAGTIIPRKDRLRRSSTQMENDPYTLVIALNSS-KAAEGELYIDDGKSYEFK-QGAFILKWEAYIFQMQPRLQ------LA--VTHFPSECTVERIILLGLSPGA
mouse       812  TLYLPVTLSSIPVFQRGGTIVPRWMRVRRSSDCMKDDPITLFVALSPQ-GTAQGELFLDDGHTFNYQTRHEFLLRRFSFSGSTLVSSS------ADP-KGHLETPIWIERVVIMG--AGK
yeast       772  HQVVPAPLGRVPVLLRGGNILITRERIRRAAELTRNDPFTLTIAVSKIGKNASGFLYLDDGVTFNYK-KGEYLIPHFSYENGILTMKDSHSNPPVSPKYSSSQKHLKVERINIYG----E

Arabidopsis 871  KSALVEPLNQKAEIEMGPLRMGGLVASSGTKVLTIRKPGVRVDQDWTVKIL
potato      873  KTALIEPGNKKVEIELGPLFIQGNRGS----VPTIRKPNVRITDDWSIQIL
mouse       992  PAAVVLQTKGSPESRLS--FQHDPETS----VLILRKPGVSVASDWSIHLR
yeast       887  QTRKSIKIRKIIDSEVTEWDVSVDDSG------CIRNPQLFLV--------
```

Figure 4

```
Arabidopsis   1   MRVVVISSFVSVSLQLSFLLLLASAIRSSSSPPNDPFLGISPQDEKYYKSSSE--IKCKDGSKKFTKAQLNDDFCDCSDGTDEPGTSACPTGKFYCRNAGHSPVILFSSRVNDGICDCCD
Rice          1   ---------MGLHAILLLLLRISASAAASRPPLD-TLGIPPQDEAYFRGG-V--IRCRDGSGRFARDKLNDDFCDCPDGTDEPGTSACPEGKFYCQNAGHSPITIFSSRVNDGICDCCD
Mouse         1   ------------MLLLLLLLPLCWAVEVKRPR-----GVSLSNHHFYEESKP--FTCLDGTATIPFDQVNDDYCDCKDGSDEPGTAACPNGSFHCTNTGYKPLYILSSRVNDGVCDCCD
Yeast         1   ----MKFSQWYTLTAPLLISSLYTVNAANDLR-----GVASDKSDLYKPDAKGNWKCLGSDKLISFNQVNDDYCDCPDGSDEPGTSACHNGKFFCKNTGYISSYIPSNRVDDTVCDCCD

Arabidopsis 119   GSDEYDGHVSCQNTCWEAGKAARENLKKKIETYNQGLVIRRQEIEQAKVGLEKDAAELKKLKSEQKILKGLVDQLKDRKEQIEKVEEKERLQKEKEEK-EKKEAELAAQQGK--GDAEEK
Rice        108   GSDEYDSNVTCKNTCWEAGKAARDKLKKKVATYKSGVVIRNQEIQKAKVAFAKDEAELAKLKGEEKILQGLVDKLTEQKKLIEKAEEEERLRKEKEEKRMKEEAEKQAADEKKASDASQE
mouse       102   GTDEYNSGTVCENTCREKGRKEKESLQQLAEVTREGFRLKKILIEEWKTAREEKQSKLLELQAGKKSLEDQVETLRAAKEEAERPEKEAKDQHRKLWEEQQAAAKARREQERAASAFQEL
yeast       111   GSD--ESLITCPNTCAQKAREYLATLEEHNRLVKNGLKIREQWALESAKKTDEVKARYKEISDSLVAVSAEKTQLSEKVEKMKRSTDLGAEAVLPSDFQDLRVALLSLVDER-----NEM

Arabidopsis 236   TDDSEKVEESSHDEGTPAVSQHDETTHHDEIGNYKDYPSDEEPAAEGEPTSILDEATHTNPADEHVVERKEESTSSEDSSSPTDESQNDGSAEKEESDEVKKVEDFVTEKKEELSKEELG
Rice        228   VDSQENHETVQEDESKVAEHHDGHATSHDNHT-----PESESSVEQHDPESQDDISIKAAPADESPPEETSAAPTKEQESTPADS--------------------------EGLSREELG
Mouse       222   DDNMDGMVSLAELQTHPELDTDGDGALSEEE------AQALLSGDTQTDTTSFYDRVWAAIRDKYRSEVPPTDIPVPEETEPKE--------------------------------EKPP
Yeast       224   QERLDILTNLLDELTLLYETDKFDETMKEAILS----FEDLKEQEIRRKVSSDDVHNYLESCNNHLSMLTGPSEDITFSSLIKD----------------------------------IK

Arabidopsis 356   RLVASRWTGEKSDKPTEADDIPKADDQENHEHTPITAHEAD-----EDDGFVSDGDEDTSDDGKYSDHEPEDDSYEEEYRHDS---SSSYKSDADDDVD-FSETTSN--PTWLEKIQKTV
Rice        317   RLVASRWTGEKVDEVSKDDKNEHEAEHDMPEHSEETHEDESDVPESAEDSYAGYHSEVEDDRHKYDDEDFSHES-DDEYVDDHDEHVASYKSDDDQKGDDHSDFTASGQASWLDKIQQTV
Mouse       304   VLPPTEEEEEEEEEPEEEEEEEEEEEEEAPPPLQPPQPPSPT-----EDEKMPPYDEET-----------------------------------------------------------
Yeast       306   KILNSLVWNIKLSLINFGILSPSASSTPLTDSES----------------------------------------------------------------------------------------

                                                                              1          2                 MHR
Arabidopsis 465   KNILLAVNLFQTTPVDKSEADRVRKEYDESSSKLNKIQSRISSLEKKLKQDFGPEKEEFYSFHGRCFESKQGKYTYKVCAYKEATQE--EGYSKTRLGEWDKFENS----YQFMSYTNGEK
Rice        436   QNVLRTFNFFKT-PVDLSEASRVRKEYDDASSKLSKIQSRISTLTDKLKHDFGKEKEEFYYFYDQCFESKEGKYVYKVCPFKKASQV--EGHSTTSLGRWDKFEES----YRVMQFSNGDR
Mouse       357   -------------QAIIDAAQEARSKFEEVERSLKEMEESIRSLEQEISFDFGPSGEEFAYLYSQCYELTTNEYVYRLCPFKLVSQKPKHGGSPTSLGTWGSWAGPDHDKFSAMKYEQGTG
Yeast       340   ----------------YRRFEAAQRDLDAAEENEKSLEKEHTKLMHELEYHHG-WDLYRAIKGMETKREIGGYTYKVVFYENVFQD------SILLGNFASQEGN------VLKYENGQS

                  3     •       4    MHR    5 •       6
Arabidopsis 579   CWNGPDRSLKVKLRCGLKNELMDVDEPSRCEYAAILSTPARCLEDKLKELQQKLEKLMNQDKP-------QNHDEL
Rice        549   CWNGPDRSLKVRLRCGLNNELNGVDEPSRCEYVAVLSTPALCDEQKLKELEQKLKASSN-----------QRHDEL
Mouse       464   CWQGPNRSTTVRLLCGKETVVTSTTEPSRCEYLMELMTPAACPEPPPEAPSD------------------GDHDEL
Yeast       431   CWNGPHRSAIVTVECGVENEIVSVLEAQKCEYLIKMKSPAACSPDQLKQSLLNTQNSANEDAVNGMEDKESSVDEL
```

Substrate recognition

Figure 5

METHODS AND MEANS FOR MODULATING CELLULOSE BIOSYNTHESIS IN FIBER PRODUCING PLANTS

This application claims priority to U.S. Provisional Application No. 60/432,674, filed on Dec. 12, 2002.

FIELD OF THE INVENTION

The invention relates to the field of agricultural biotechnology. More specifically, the invention provides novel genes involved in cellulose biosynthesis and methods using such genes to modulate cellulose biosynthesis in fiber-producing plants such as cotton. The invention also provides methods for identifying and isolating alleles of these genes in a population of fiber producing plants that correlate with the quality of the produced fibers.

BACKGROUND

Cellulose is the major structural polysaccharide of higher plant cell walls. Chains of β-1,4-linked glucosyl residues assemble soon after synthesis to form rigid, chemically resistant microfibrils. Their mechanical properties together with their orientation in the wall influence the relative expansion of cells in different directions and determine many of the final mechanical properties of mature cells and organs. These mechanical properties are of great importance for wood, paper, textile and chemical industries.

Much of the high quality fiber for the textile industry is provided for by cotton. About 90% of cotton grown worldwide is *Gossypium hirsutum* L., whereas *Gossypium barbadense* accounts for about 8%.

Several genes involved in cellulose biosynthesis have already been identified by mutational analysis in a number of plants. Mutants of *Arabidopsis thaliana* show that in vivo cellulose synthesis requires the activity of members of the AtCesA gene family encoding glycosyltransferases (Arioli et al., 1998; Taylor et al., 1999; Fagard et al., 2000; Taylor et al., 2000; Scheible et al., 2001; Burn et al., 2002a; Desprez et al., 2002), of the AtKOR1 gene (At5g49720) encoding a membrane-associated endo-1,4-β-D-glucanase (Nicol et al., 1998; Zuo et al., 2000; Lane et al., 2001; Sato et al., 2001), of KOBITO1 encoding a plasma membrane protein of unknown function (Pagant et al., 2002) and of genes encoding enzymes in the N-glycosylation/quality control pathway in the ER (Lukowitz et al., 2001; Burn et al., 2002b; Gillmor et al., 2002).

The function of an endo-1,4-β-D-glucanase in cellulose synthesis remains to be determined but the lack of activity against crystalline cellulose of BnCel16, a related *Brassica napus* enzyme (Mølhøj et al., 2001), suggests that the enzyme probably cleaves a non-crystalline glucan chain such as a lipid-linked primer or glucan donor (Williamson et al., 2001; Peng et al., 2002). Tomato Cel3 (LeCel3) was the first such membrane-associated endo-1,4-β-D-glucanase identified (Brummell et al., 1997) and antibodies to LeCel3 detected a cotton fiber protein upregulated during herbicide inhibition of cellulose synthesis (Peng et al., 2001). A cotton fiber membrane fraction required $Ca^{2+}$ for in vitro cellulose synthesis activity and, because an exogenous, $Ca^{2+}$-independent endo-1,4-β-D-glucanase restored cellulose synthesis activity, a cotton orthologue of KOR (GhKOR) was proposed as the endogenous $Ca^{2+}$-dependent factor (Peng et al., 2002). A truncated form of BnCel16 showed $Ca^{2+}$-dependence in vitro (Mølhøj et al., 2001).

Further genetic data point to cellulose synthesis responding to defects in enzymes on the N-glycosylation/quality control pathway. These steps occur in the ER rather than at the plasma membrane and so probably act only indirectly on synthesis through the supply of key glycoproteins to the plasma membrane. N-glycosylation begins when the mannose-rich oligosaccharide Glc3Man9GlcNac2 is assembled on dolichol in the ER membrane and transferred to the Asn residue of a newly synthesized protein containing an Asn-X-Ser or Asn-X-Thr motif (where X is any amino acid except Pro).

With further processing of the glycoprotein by glucosidases I and II, N-glycosylation intersects with the quality control pathway responsible for ensuring proper folding of newly synthesized proteins (Helenius and Aebi, 2001; Vitale, 2001). Glucosidase I removes the terminal α-1,2-linked glucosyl residue to generate Glc2Man9GlcNac2 and glucosidase II removes the next α-1,3-glucosyl residue. Polypeptides carrying the resultant GlcMan9GlcNac2 specifically bind chaperones (calnexin and calreticulin) and probably other proteins that promote proper folding of newly synthesized proteins. The glycoprotein releases the chaperones when glucosidase II trims of the final Glc residue which is required for chaperone binding. Glycoprotein glucosyltransferase then reattaches one Glc residue to the Man9GlcNAc2 of improperly folded glycoproteins so that they again bind chaperones and have a further opportunity to fold properly. Properly folded proteins, however, cannot be reglucosylated by that enzyme and progress though the secretory pathway for further processing and delivery.

Defects at several points in this pathway affect cellulose synthesis. Sequence analysis suggests that the potato MAL1 gene encodes a glucosidase II and antisense suppression reduces glucosidase II activity (Taylor et al, 2000a).M4LJ antisense plants accumulate less cellulose than controls when grown under field conditions although there is no visible phenotype in glasshouse conditions. The embryo lethal knopf mutant is deficient in glucosidase I and severely deficient in cellulose (Gillmor et al., 2002). Finally the embryo lethal cyt1 mutant is cellulose-deficient from a defect in mannose-1-phosphate guanylyltransferase, the enzyme generating the UDP-Man required to (amongst other things) assemble the high mannose oligosaccharide that is transferred from dolichol to the nascent protein (Lukowitz et al, 2001). The mutations that affect cellulose synthesis concentrate towards those early steps where the N-glycosylation pathway intersects with the quality control pathway. Quality control, rather than production of mature glycans on critical proteins, seems particularly important since there is no detectable phenotype from a defect in N-acetyl glucosaminyl transferase I that blocks the steps in the Golgi that build mature, N-linked glycans (von Schaewen et al, 1993).

Baskin et al. 1992 described *Arabidopsis* mutants which show root radial swelling, named rsw1, rsw2 and rsw3. These mutant lines where shown to exhibit a selective reduction in cellulose production (Peng et al. 2000).

WO98/00549 relates generally to isolated genes which encode polypeptides involved in cellulose biosynthesis in plants and transgenic plants expressing same in sense or antisense orientation, or as ribozymes, co-suppression or gene-targeting molecules. More particularly, this disclosure is directed to a nucleic acid molecule isolated from *Arabidopsis thaliana, Oryza sativa*, wheat, barley, maize, *Brassica* spp. *Gossypium hirsutum* and *Eucalyptus* spp, which encode an enzyme which is important in cellulose biosynthesis, in particular the cellulose synthase enzyme and homologues, analogues and derivatives thereof and uses of same in the production of transgenic plants expressing altered cellulose biosynthetic properties.

WO 98/50568 discloses the use of a nucleotide sequence coding for an endo-1,4-β-glucanase to inhibit cell growth in a plant. The nucleotide sequence corresponds wholly or partially to the *Arabidopsis* KOR protein sequence, or to a protein sequence the N-terminal end of which has at least 40% identity with the first 107 amino acids of said KOR, or at least 70% identity with the first 107 amino acids of said KOR.

WO 97/24448 describes recombinant and isolated nucleic acids encoding a plant α-glucosidase enzyme. An antisense nucleotide was also provided as well as the use of both the isolated or recombinant sequences and the antisense sequences. Uses of the invention include enhancing and reducing expression of alpha-glucosidases and the provision of novel starches.

WO 00/08175 relates to nucleic acid molecules coding for a protein with the activity of an alpha-glucosidase from a potato. The invention also relates to methods for the production of transgenic plant cells and plants synthesizing modified starch. The invention further relates to vectors and host cells containing the nucleic acid molecules, plant cells and plants obtained according to the methods, starch synthesized by the described plant cells and methods for the production of such starch.

WO 98/39455 discloses a gene and enzyme participating in the synthesis of cellulose by microorganisms. A specific gene encoding a cellulase, cellulose synthase complex and alpha-glucosidase are described.

WO9818949 and U.S. Pat. No. 6,271,443 provide two plant cDNA clones that are homologs of the bacterial CelA genes that encode the catalytic subunit of cellulose synthase, derived from cotton (*Gossypium hirsutum*). Also provided are genomic promoter regions to these encoding regions to cellulose synthase. Methods for using cellulose synthase in cotton fiber and wood quality modification are also provided.

The prior art remains however deficient in providing alternatives to the known genes involved in cellulose biosynthesis and does not disclose the nucleotide sequence of the wild type gene involved in cellulose biosynthesis and mutated in the rsw3 mutant *Arabidopsis* line. Also, the prior art does not disclose the cotton homologues genes of RSW2 or RSW3 involved in cellulose biosynthesis from cotton.

These and other problems have been solved as set forth hereinafter in the different embodiments and claims of the invention.

SUMMARY OF THE INVENTION

It is one object of the invention to provide a method for increasing cellulose biosynthesis e.g. in lint fiber, in fiber-producing plants, such as cotton plants, comprising the steps of (a) providing cells of said fiber-producing plant with a chimeric gene comprising the following operably linked DNA fragments i) a promoter expressible in said cell of said plant, such as a constitutive promoter, a fiber specific promoter or an expansin promoter;

ii) a DNA region coding for the protein comprising the amino acid sequence of SEQ ID No. 5 or SEQ ID No 6 or SEQ ID No 7 or SEQ ID No 8 (or a variant of that protein having the same enzymatic activity), such as the nucleotide sequence of SEQ ID No 1 from the nucleotide at position to the nucleotide at position 1986 or SEQ ID No. 2 from the nucleotide position 47 to the nucleotide at position 1906 or SEQ ID No 3 or SEQ ID No 4 from the nucleotide position 2 to the nucleotide at position 1576 or SEQ ID No. 9;

iii) a 3' region involved in transcription termination and polyadenylation.

It is another object of the invention to provide a method for decreasing cellulose biosynthesis in fiber-producing plants, for example in cotton plants, e.g. in fuzz fiber, comprising the step of providing cells of said fiber-producing plant with a chimeric gene capable of reducing the expression of a gene endogenous to said fiber-producing plant, wherein said endogenous gene codes for a protein comprising the amino acid sequence of SEQ ID No. 5 or SEQ ID No 6 or SEQ ID No 7 or SEQ ID No 8 or a variant thereof, said variant having the same enzymatic activity. The introduced chimeric gene may comprise a nucleotide sequence of 21 contiguous nucleotides selected from a nucleotide sequence which codes for a protein comprising the amino acid sequence of SEQ ID No. 5 or SEQ ID No 6 or SEQ ID No 7 or SEQ ID No 8, such as the nucleotide sequence of SEQ ID No 1 or SEQ ID No. 2 or SEQ ID No 3 or SEQ ID No 4 or SEQ ID No. 9, or the complement thereof, operably linked to a plant expressible promoter, such as a constitutive promoter or a fuzz fiber specific promoter and a 3' region involved in transcription termination and polyadenylation. The chimeric gene may also comprise a first nucleotide sequence of 21 contiguous nucleotides selected from a nucleotide sequence which codes for a protein comprising the amino acid sequence of SEQ ID No. 5 or SEQ ID No 6 or SEQ ID No 7 or SEQ ID No 8, such as the nucleotide sequence of SEQ ID No. 1, SEQ ID No. 2, SEQ ID No. 3 and SEQ ID No. 4 or SEQ ID No. 9, and a second nucleotide sequence complementary to the first nucleotide sequence, operably linked to a plant expressible promoter and a 3' region involved in transcription termination and polyadenylation such that upon transcription of said chimeric gene, a RNA is formed which can form a double stranded RNA region between said first and said second nucleotide sequence.

The invention further relates to a chimeric gene for increasing cellulose biosynthesis in fiber-producing plants, e.g. in cotton plants, comprising the following operably linked DNA fragments: a promoter expressible in said cell of said plant such as a constitutive promoter, a (lint)-fiber specific promoter or an expansin promoter; a DNA region coding for the protein comprising the amino acid sequence of SEQ ID No 6 or SEQ ID No 7 or SEQ ID No 8 or a variant thereof, said variant having the same enzymatic activity, such as the nucleotide sequence of SEQ ID No. 1 from the nucleotide at position 121 to the nucleotide at position 1986 or SEQ ID No 2 from the nucleotide at position 47 to the nucleotide at position 1906 or SEQ ID No 3 or SEQ ID No 4 from the nucleotide at position 2 to the nucleotide at position 1576 or SEQ ID No. 9; and a 3'end region involved in transcription termination and polyadenylation.

The invention also relates to a chimeric gene for decreasing cellulose biosynthesis in fiber-producing plants, e.g. in cotton plants, comprising a nucleotide sequence of 21 contiguous nucleotides selected from a nucleotide sequence which codes for a protein comprising the amino acid sequence of SEQ ID No 6 or SEQ ID No 7 or SEQ ID No 8, such as the nucleotide sequence of SEQ ID No. 2, SEQ ID No. 3 or SEQ ID No. 4 or SEQ ID No. 9, or the complement thereof, operably linked to a plant expressible promoter and a 3' region involved in transcription termination and polyadenylation.

The invention further relates to a chimeric gene for decreasing cellulose biosynthesis in fiber-producing plants, e.g. in cotton plants, comprising a first nucleotide sequence of 21 contiguous nucleotides selected from a nucleotide sequence which codes for a protein comprising the amino acid sequence of SEQ ID No 6 or SEQ ID No 7 or SEQ ID No 8, and a second nucleotide sequence complementary to said first nucleotide sequence, operably linked to a plant expressible promoter and a 3' region involved in transcription termination and polyadenylation such that upon transcription of said chimeric gene, a RNA is formed which can form a double stranded RNA region between said first and said second nucleotide sequence.

It is yet another object of the invention to provide plant cells and plants comprising the chimeric genes of the invention as well as seeds of such plants comprising the chimeric genes of the invention.

The invention thus relates to the use of a chimeric gene according to the invention to modulate cellulose biosynthesis and fiber quality in a fiber producing plant, such as cotton.

It is also an object of the invention to provide a method for identifying allelic variations of the genes encoding proteins involved in cellulose biosynthesis in a population of different genotypes or varieties of a particular plant species, for example a fiber-producing plant species, which are correlated either alone or in combination with the quantity and/or quality of cellulose production, and fiber production comprising the steps of:

a) providing a population of different varieties or genotypes of a particular plant species or interbreeding plant species comprising different allelic forms of the nucleotide sequences encoding proteins comprising the amino acid sequences of SEQ ID No 5, 6, 7 or 8;
b) determining parameters related to fiber production and/or cellulose biosynthesis for each individual of the population;
c) determining the presence (or absence) of a particular allelic form of the nucleotide sequences encoding proteins comprising the amino acid sequences of SEQ ID No 5, 6, 7 or 8 for each individual of the population; and
d) correlating the occurrence of particular fiber or cellulose parameters with the presence of a particular allelic form of the mentioned nucleotide sequence or a particular combination of such allelic forms.

BRIEF DESCRIPTION OF THE FIGURES

FIG. 4. Alignment of the Aglu-3/RSW3 sequence (Genbank NP_201189; SEQ ID NO 26) with the sequences of ER-resident glucosidase II enzymes from potato (Accession number T07391; SEQ ID NO 27), mouse (NP_032086; SEQ ID NO 28) and fission yeast (CAB65603; SEQ ID NO 29). The clade 2 of Monroe et al. (1999)are shown to demonstrate the high conservation. They include several residues implicated in catalysis (Asp 512 and Asp 617; *). The site of the rsw3-1 mutation(Ser 599●) is close to these consensus sequences and is conserved in these and other glucosidase II sequences. Predicted N-terminal signal sequences are boxed. No HDEL ER-retention sequences occur at the C-terminus.

FIG. 5. Alignments of the proposed β-subunits of *Arabidopsis* (At5g56360; SEQ ID NO 30) and rice (our amendment of BAA88186; SEQ ID NO 31) with the β-subunits of glucosidase II from mouse (AAC53183; SEQ ID NO 32) and fission yeast (BAA1 3906; SEQ ID NO 33). Note the predicted N-terminal signal sequences (boxed), C-terminal HNDEL ER-retention signals and the mannose-receptor homology region (MHR) near the N-terminus. The 6 cysteines within the MHR (four only in yeast) are numbered and the R and Y residues implicated in substrate-binding (●) and the substrate recognition loop between cysteines 5 and 6 are marked. Elsewhere in the sequence, note the relatively high level of similarity in the N- and C-terminal domains and the much lower similarity and plant-specific inserts in the central region.

(a) Root system of a seedling showing that lateral roots extend some distance before swelling and stopping elongation. Plants grown 5 d at 21° C. and 6 d at 30° C. Scale bar=2 mm.
(b) Continued root growth gives a dense, highly branched root system and a dense mass of very small leaves on a plant grown for 21 d at 30° C. Scale bar=5 mm.
(c) Hypocotyls grown in the dark for 3 d at 21° C. and 3 d at 30° C. From the left: wildtype, rsw1-1, rsw2-1, rsw3, rsw1-1rsw2-1, rsw1-1rsw3. The rsw3 effect on the hypocotyl is weak compared to that of the other single mutants and rsw1-1rsw3 is weaker than rsw1-1rsw2-1. Scale bar=5 mm.
(d) Light micrograph of rsw3 grown on agar for 35 d at 30° C. Tiny inflorescences with flower buds of near normal size (top right and bottom left) emerge from several of the rosettes. Scale bar=5 mm.

(e) Scanning electron micrograph of rsw3 plant grown for 21 d at 30° C. and showing the presence of multiple rosettes. Scale bar=1 mm.

(f) Detail of the ringed area in (e) showing the very complex arrangement of the minute leaves, many of which carry trichomes of approximately normal size and morphology. Scale bar=200 μm.

(g) Scanning electron micrograph of the surface of a wild type leaf on a plant grown for 10 d at 30° C. Note the clearly defined cell boundaries, stomata and trichomes.

(h) The surface of an rsw3 leaf showing much less clear outlines to the pavement cells, an apparently collapsed trichome (CT) on top of its ring of subsidiary cells and many stomata with their guard cells protruding above the leaf surface. Scale bar for (g) and (h)=100 μm.

Figure 8:
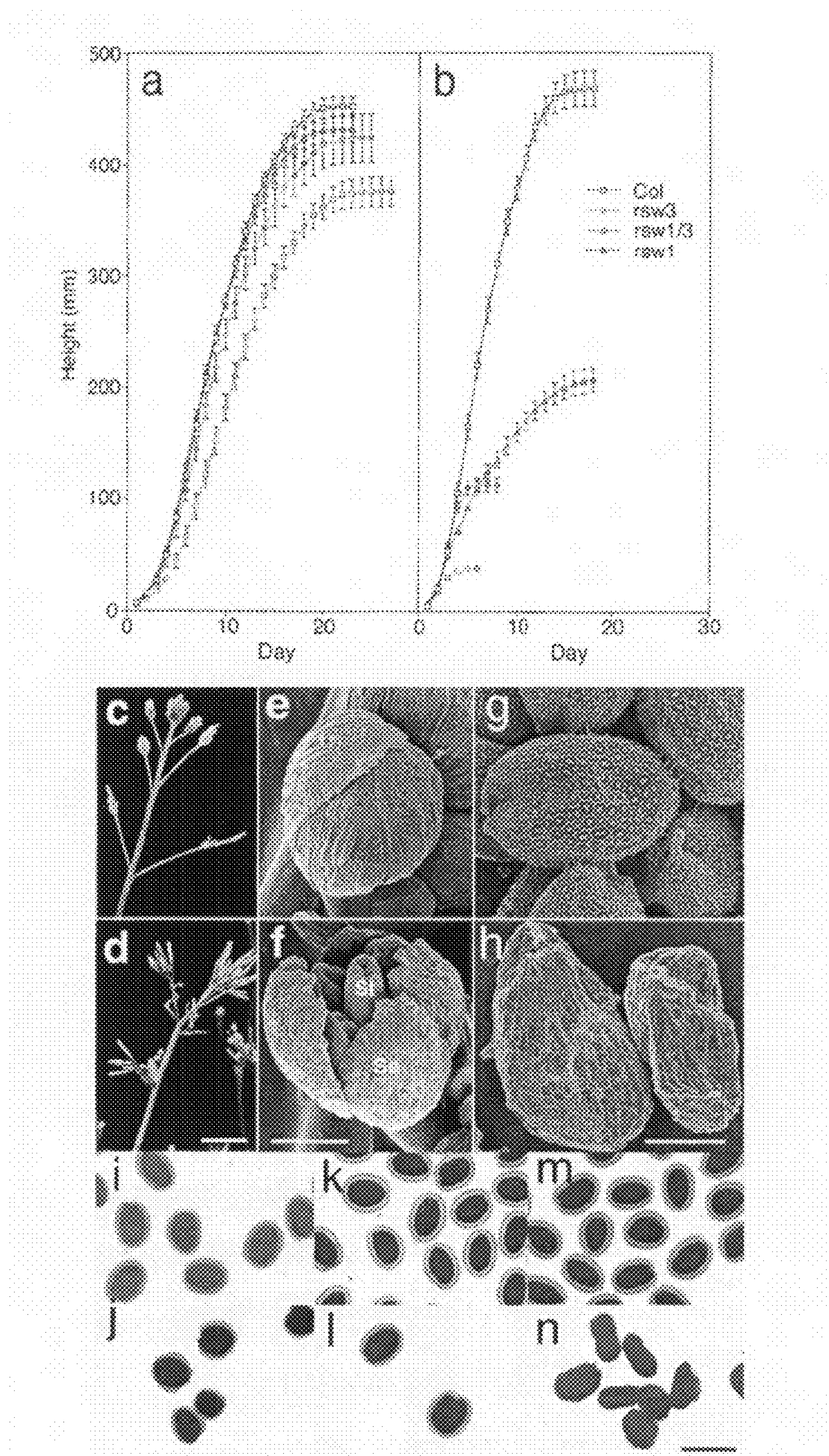

FIG. 8. Growth of the stem and reproductive development in rsw3.

(a and b) Kinetics of secondary stem elongation in Columbia wild type, rsw3, rsw1 and the rsw1rsw3 double mutant at 21° C. (a) and 30° C. (b). All plants were grown at 21° C. until stems began to emerge. These were cut off and re-growth of secondary bolts followed at the indicated temperature. Single mutants show very little difference from wild type at 21° C. although the double mutant elongates more slowly and reaches a significantly shorter final height. The final heights reached at 30° C. differ widely as do the trajectories by which they are reached. rsw1 elongates more slowly but elongation continues for at least as long as it does in wild type. rsw3 elongates almost as rapidly as wild type for 4 d but then ceases elongation by about day 6. The rsw1rsw3 double mutant elongates less rapidly and ceases elongation at about day 5.

(c and d). Light micrographs showing well spaced flowers in wild type (c) and the clustered flowers on rsw3 (d) with its early cessation of elongation.

(e and f) Cryoscanning electron micrographs showing flower buds of wild type (e) and rsw3 (f) that are of similar sizes but open prematurely in rsw3. Note the immature state of the stigma (St) and the irregular shapes of the cells on the sepals (Se) in rsw3. Bar for (e) and (f)=200 μm.

(g and h) Cryo-scanning electron micrographs showing imbibed seed of rsw3 that developed on plants held at 21° C. (g) and 30° C. (h). The 30° C. seed is shrunken and lacks the clear cellular pattern of the 21° C. seed.

(i-n) Light micrographs of imbibed seed stained with ruthenium red to show a surface coat of mucilage. Wild type (i,j), rsw1 (k,l), rsw3 (m,n). Seed in i, k, m developed on plants at 21° C., seed in j, l, n developed on plants at 30° C. Mucilage is secreted normally by rsw1 (l) and wild type (j) at 30° C. but not by rsw3(n).

DETAILED DESCRIPTION

The invention is based on the identification of the wild type gene which has been mutated in *Arabidopsis* mutant rsw3, and elucidation of its function. The inventors have also identified the cotton genes corresponding to the genes mutated in rsw2 and rsw3 *Arabidopsis* mutants. These cotton genes are implicated in cellulose production.

In one embodiment the invention thus relates to a method for increasing the production of cellulose in a plant comprising the steps of providing cells of the plant with a chimeric gene comprising a plant-expressible promoter operably linked to a DNA region coding for a protein comprising the amino acid sequence of SEQ ID No 5, SEQ ID No. 6, SEQ ID No 7 or SEQ ID No 8 or a variant thereof having similar activity as the mentioned proteins, and a 3' region involved in transcription termination and polyadenylation. The plants may be fiber-producing plants such as cotton, and the increased cellulose production may result in a larger production of cotton fibers, e.g. cotton lint fibers, or in cotton fibers with altered or increased length, or altered quality such as improved tensile strength.

As used herein, "chimeric gene" or "chimeric nucleic acid" refers to any gene or any nucleic acid, which is not normally found in a particular eukaryotic species or, alternatively, any gene in which the promoter is not associated in nature with part or all of the transcribed DNA region or with at least one other regulatory region of the gene.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind. The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

In one embodiment of the invention the promoter is a constitutive promoter. In another embodiment of the invention, the promoter activity is enhanced by external or internal stimuli (inducible promoter), such as but not limited to hormones, chemical compounds, mechanical impulses, abiotic or biotic stress conditions. The activity of the promoter may also be regulated in a temporal or spatial manner (tissue-specific promoters; developmentally regulated promoters).

In a particular embodiment of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Hapster et al., 1988), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al.,1989), tuber-specific promoters (Keil et al., 1989), vascular tissue specific promoters (Peleman et al., 1989), stamen-selective promoters (WO 89/10396, WO 92/13956), and the like.

Suitable plant-expressible promoters include the fiber specific and/or secondary cell wall specific promoters which can be isolated according to the teaching of WO 98/18949, WO98/00549 or U.S. Pat. No. 5,932,713. Also suitable are the promoters disclosed in WO98/18949 or U.S. Pat. No. 6,271,443. Cotton lint-fiber specific promoters are also suitable.

In one embodiment of the above mentioned methods, the DNA region coding for a protein comprising the amino acid sequence of SEQ ID No 5, SEQ ID No 6, SEQ ID No 7 or SEQ ID No 8 comprises the nucleotide sequence of SEQ ID No 1 from nucleotide 121 to nucleotide 1986, SEQ ID No 2 from nucleotide 47 to nucleotide 1906, SEQ ID No. 3 or SEQ ID No. 4 from nucleotide 2 to nucleotide 1576 or SEQ ID No. 9.

In another embodiment of the above mentioned methods, the DNA region codes for a variant of the proteins comprising the amino acid sequence of SEQ ID No. 5, SEQ ID No. 6, SEQ ID No. 7 or SEQ ID No. 8. As used herein, “variant” proteins refer to proteins wherein one or more amino acids are different from the corresponding position in the proteins having the amino acid sequence of SEQ ID No. 5, SEQ ID No. 6, SEQ ID No. 7 or SEQ ID No. 8, by substitution, deletion, insertion; and which have at least one of the functions of the proteins encoded by SEQ ID No. 5, SEQ ID No. 6, SEQ ID No. 7 or SEQ ID No. 8 such as e.g. the same enzymatic or catalytic activity. Methods to derive variants such as site-specific mutagenesis methods are well known in the art, as well as assays to identify the enzymatic activity encoded by the variant sequences. Suitable substitutions include, but are not limited to, so-called conservative substitutions in which one amino acid residue in a polypeptide is replaced with another naturally occurring amino acid of similar chemical character, for example Gly⇔Ala, Val⇔Ile⇔Leu, Asp⇔Glu, Lys⇔Arg, Asn⇔Gln or Phe⇔Trp⇔Tyr.

Allelic forms of the nucleotide sequences which may encode variant proteins, according to the specification may be identified by hybridization of libraries, under stringent conditions, such as cDNA or genomic libraries of a different varieties or plant lines, e.g. cotton varieties and plant lines. Nucleotide sequences which hybridize under stringent conditions to nucleotide sequences encoding the amino acid sequence of SEQ ID 5, 6, 7 or 8 or to the nucleotide sequence of SEQ ID 1, 2, 3, 4 or 9, or a sufficiently large part thereof (e.g., at least about 25 contiguous nucleotides, at least about 50 contiguous nucleotides, or at least about 100 contiguous nucleotides) and which encode a functional protein that can complement at least one function, and may complement all of the affected functions, in the rsw2 or rsw3 mutant line in *Arabidopsis* are functional equivalents of the above mentioned coding regions. Such nucleotides may also be identified and isolated using e.g. polymerase chain reaction amplification using an appropriate pair of oligonucleotides having at least about 25 contiguous nucleotides, at least about 50 contiguous nucleotides, or at least about 100 contiguous nucleotides of the nucleotide of SEQ ID No 1, SEQ ID No 2, SEQ ID No. 3, SEQ ID No 4 or SEQ ID No. 9.

“Stringent hybridization conditions” as used herein mean that hybridization will generally occur if there is at least 95%, or at least 97%, sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt’s solution, 10% dextran sulfate, and 20 μg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

As another aspect of the invention, the identified genes may be used to decrease cellulose biosynthesis in plants such as fiber-producing plants, e.g. cotton. Thus, in another embodiment of the invention, a method is provided to decrease cellulose biosynthesis in plants such as fiber-producing plants, e.g. in cotton plants, comprising the step of providing cells of said fiber-producing plant with a chimeric gene capable of reducing the expression of a gene endogenous to said fiber-producing plant, wherein said endogenous gene codes for a protein comprising the amino acid sequence of SEQ ID No. 5 or SEQ ID No 6 or SEQ ID No 7 or SEQ ID No 8 or a variant thereof, said variant having the same functional or enzymatic activity.

In one embodiment of this method of the invention, a chimeric gene is provided to cells of the plant, wherein the chimeric gene comprises a nucleotide sequence of 21 contiguous nucleotides selected from a nucleotide sequence which codes for a protein comprising the amino acid sequence of SEQ ID No. 5 or SEQ ID No 6 or SEQ ID No 7 or SEQ ID No 8, such as a nucleotide sequence of 21 contiguous nucleotides selected from the nucleotide sequences of SEQ ID No. 1 or SEQ ID No 2 or SEQ ID No 3 or SEQ ID No 4 or SEQ ID No. 9 operably linked to a plant expressible promoter and a 3' region involved in transcription termination and polyadenylation (so-called “sense” RNA mediated gene silencing). In another embodiment of this method of the invention, a chimeric gene is provided to cells of the plant, wherein the chimeric gene comprises a nucleotide sequence of 21 contiguous nucleotides selected from the complement of a nucleotide sequence which codes for a protein comprising the amino acid sequence of SEQ ID No. 5 or SEQ ID No 6 or SEQ ID No 7 or SEQ ID No 8, such as a nucleotide sequence of 21 contiguous nucleotides selected from the complement of the nucleotide sequences of SEQ ID No. 1 or SEQ ID No 2 or SEQ ID No 3 or SEQ ID No 4 or SEQ ID No. 9 operably linked to a plant expressible promoter and a 3' region involved in transcription termination and polyadenylation (so-called “antisense” RNA mediated gene silencing).

The length of the antisense or sense nucleotide sequence may vary from about 21 nucleotides (nt), up to a length equaling the length (in nucleotides) of the target nucleic acid. The total length of the antisense or sense nucleotide sequence may be at least about 50 nt, 100 nt, 150 nt, 200 nt, or 500 nt long. It is expected that there is no upper limit to the total length of the antisense nucleotide or sense nucleotide sequence, other than the total length of the target nucleic acid. However for practical reason (such as, e.g., stability of the chimeric genes) the length of the antisense or sense nucleotide sequence may be limited to 5000 nt, to 2500 nt, or even to about 1000 nt.

It will be appreciated that the longer the total length of the antisense or sense nucleotide sequence is, the less stringent the requirements for sequence identity between the total antisense or sense nucleotide sequence and the corresponding sequence in the target gene or the complement thereof become. In one embodiment, the total antisense nucleotide sequence will have a sequence identity of at least about 75% with the complement corresponding target sequence; alternatively, at least about 80%, at least about 85%, about 90%, about 95%, about 100%, or is identical to complement of the corresponding part of the target nucleic acid. In one embodiment, the antisense or sense nucleotide sequence will include a sequence of about 20-21 nt with 100% sequence identity to the corresponding part of the target nucleic acid or the complement thereof. For calculating the sequence identity and designing the corresponding antisense or sense sequence, the number of gaps may be minimized, particularly for the shorter antisense or sense sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The alignment of the two sequences may be performed by the Needleman and Wunsch algorithm (Needleman and Wunsch, 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Another embodiment of the invention, relates to a method for reducing the expression of endogenous genes of said fiber-producing plant, wherein said endogenous gene codes for a protein comprising the amino acid sequence of SEQ ID No. 5 or SEQ ID No 6 or SEQ ID No 7 or SEQ ID No 8 or a variant thereof using DNA regions, under the control of a plant-expressible promoter, which when transcribed result in so-called double stranded RNA molecules, comprising both sense and antisense sequences which are capable of forming a double stranded RNA molecule as described in WO 99/53050 (herein entirely incorporated by reference).

Thus, in one embodiment of the invention, a chimeric gene may be provided to a plant cell comprising a plant expressible promoter operably linked to a DNA region, whereby that DNA region comprises a part of coding region comprising at least 20 or 21 consecutive nucleotides from the coding region of a nucleic acid encoding a protein with the amino acid sequence of SEQ ID Nos 5, 6, 7 or 8 (the so-called sense part) as well as a DNA sequence that comprises at least the complementary DNA sequence of at least 20 or 21 nucleotides of the sense part, but which may be completely complementary to the sense part (the so-called antisense part). The chimeric gene may comprise additional regions, such as a transcription termination and polyadenylation region functional in plants. When transcribed an RNA can be produced which may form a double stranded RNA stem between the complementary parts of the sense and antisense region. A spacer region may be present between the sense and antisense nucleotide sequence. The chimeric gene may further comprise an intron sequence, which may be located in the spacer region.

In yet another embodiment of the invention, the chimeric gene used to reduce the expression of a gene endogenous to said fiber-producing plant, wherein said endogenous gene codes for a protein comprising the amino acid sequence of SEQ ID No. 5 or SEQ ID No 6 or SEQ ID No 7 or SEQ ID No 8 or a variant thereof, said variant having the same functional or enzymatic activity, encodes a ribozyme which recognizes and cleaves RNA having the nucleotide sequence of an RNA coding for a protein comprising the amino acid sequence of SEQ ID No. 5 or SEQ ID No 6 or SEQ ID No 7 or SEQ ID No 8 or a variant thereof. In another embodiment, the ribozyme recognizes and cleaves RNA having the nucleotide sequence of an RNA comprising the nucleotide sequence of SEQ ID 1, 2, 3 or 4. Methods for designing and using ribozymes have been described by Haseloff and Gerlach (1988) and are contained i.a. in WO 89/05852.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application. In yet another embodiment of the invention, nucleic acids (either DNA or RNA molecules) are provided which can be used to alter cellulose biosynthesis in plants. Thus the invention provides chimeric genes (DNA molecule) which comprise the following operably linked DNA fragments i) a promoter expressible in said cell of said plant;
ii) a DNA region comprising a nucleotide sequence of at least 21 nucleotides selected from a nucleotide sequence coding for the protein comprising the amino acid sequence of SEQ ID No 6 or SEQ ID No 7 or SEQ ID No 8 (or a variant of that protein having the same enzymatic activity), such as the nucleotide sequence of SEQ ID Nos 1, 2, 3, 4 or 9; and/or
iii) a DNA region and comprising a nucleotide sequence of at least 21 nucleotides selected from the complement of a nucleotide sequence coding for the protein comprising the amino acid sequence of SEQ ID No 6 or SEQ ID No 7 or SEQ ID No 8 or a variant thereof, said variant having the same enzymatic activity, such as the nucleotide sequence of SEQ ID Nos 1, 2, 3, 4 or 9; and
iv) a 3'end region involved in transcription termination and polyadenylation.

Also provided are RNA molecules that can be obtained from the chimeric genes according to the invention. Such RNA molecules can be produced by in vivo or in vitro transcription of the chimeric genes. They can also be obtained through in vitro transcription of chimeric genes, wherein the transcribed region is under control of a promoter recognized by single subunit RNA polymerases from bacteriophages such as SP6, T3 or T7. Alternatively, the RNA molecules may be synthesized in vitro using procedures well known in the art. Also chemical modifications in the RNA ribonucleoside backbone to make the chimeric RNA molecules more stable are well known in the art.

Different embodiments for chimeric genes or RNA molecules have been described above in relation to the provided methods for altering cellulose biosynthesis and can be applied mutatis mutandis to the embodiments relating to substances.

Chimeric genes or RNA may be provided to plant cells in a stable way, or transiently. Conveniently, stable provision of chimeric genes or RNA molecules may be achieved by integration of the chimeric genes into the genome of the cells of a plant. Methods for the introduction of chimeric genes into plants are well known in the art and include *Agrobacterium*-mediated transformation, particle gun delivery, microinjection, electroporation of intact cells, polyethylene glycol-mediated protoplast transformation, electroporation of protoplasts, liposome-mediated transformation, silicon-whiskers mediated transformation etc. The transformed cells obtained in this way may then be regenerated into mature fertile plants.

In another embodiment, the chimeric genes or chimeric RNA molecules of the invention may be provided on a DNA or RNA molecule capable of autonomously replicating in the cells of the plant, such as e.g. viral vectors. The chimeric gene or the RNA molecules of the invention may also be provided transiently to the cells of the plant.

It is also an object of the invention to provide plant cells and plants containing the chimeric genes or the RNA molecules according to the invention. Gametes, seeds, embryos, either zygotic or somatic, progeny or hybrids of plants comprising the chimeric genes of the present invention, which are produced by traditional breeding methods, are also included within the scope of the present invention.

The methods and means of the invention are suited for use in cotton plants, (both *Gossypium hirsutum* and *Gossypium barbadense*) including, but not limited to, plants such as Coker 312, Coker310, Coker 5Acala SJ-5, GSC25110, FiberMax®819, FiberMax®832, FiberMax® 966, FiberMax® 958, FiberMax® 989, FiberMax® 5024 (and transgenic FiberMax® varieties exhibiting herbicide or insect-resistant traits) Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA.

The methods and means described herein may also be employed for other plant species such as hemp, jute, flax and woody plants, including but not limited to *Pinus* spp., *Populus* spp., *Picea* spp., *Eucalyptus* spp., etc.

In another embodiment, a method for identifying allelic variations of the genes encoding proteins involved in cellulose biosynthesis in a population of different genotypes or varieties of a particular plant species, for example a fiber-producing plant species, which are correlated either alone or in combination with the quantity and/or quality of cellulose production, and fiber production is provided. This method comprises the following steps:

a) providing a population of different varieties or genotypes of a particular plant species or interbreeding plant species comprising different allelic forms of the nucleotide sequences encoding proteins comprising the amino acid sequences of SEQ ID No 5, 6, 7 or 8. The different allelic forms may be identified using the methods described elsewhere in this application. For example, a segregating population may be provided, wherein different combinations of the allelic variations of the genes encoding proteins involved in cellulose biosynthesis are present. Methods to produce segregating populations are well known in the art of plant breeding.
b) Determining parameters related to fiber production and/or cellulose biosynthesis for each individual of the population;
c) determining the presence of a particular allelic form of the nucleotide sequences encoding proteins comprising the amino acid sequences of SEQ ID No 5, 6, 7 or 8 for each individual of the population; and
d) correlating the occurrence of particular fiber or cellulose parameters with the presence of a particular allelic form of the mentioned nucleotide sequence or a particular combination of such allelic forms.

The resulting information will allow selecting those alleles which have the desired effect on cellulose biosynthesis or fiber production. The resulting information may be used to accelerate breeding programs, to isolate or create varieties with particular fiber or cellulose characteristics, or to accelerate backcross programs, by determining the presence or absence of allelic forms, using conventional molecular biology techniques. Methods for determining allelic forms in polyploid plants are known in the art and include e.g. Denaturing High-Performance Liquid Chromatography (DHPLC; Underhill et al. (1997) *Genome Research* 7:996-1005). It will be clear that not only the sequences of the alleles themselves can be used to determine their presence or absence during breeding or backcross programs, but also of the nucleotide sequences adjacent (e.g., immediately adjacent) and contiguous with the desired alleles, and which can only be separated from the allele by recombination during meiosis at low frequencies during meiosis.

As used herein "an interbreeding plant species" is a species which can be crossed with the fiber producing plant such as cotton (including using techniques such as hybridization etc.) and can produce progeny plants. Interbreeding plant species may include wild relatives of the fiber producing plants. Conventionally, for cotton plants reference is made to interbreeding for crosses between *G. barbadense* and *G. hirsutum* and to intrabreeding for crosses between two *G. barbadense* or two *G. hirsutum* parents.

The following non-limiting Examples describe method and means for modulating cellulose biosynthesis in fiber-producing plants. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology*, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) *Molecular Cloning: A Laboratory Manual*, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany.

Throughout the description and Examples, reference is made to the following sequences:

SEQ ID No.1: *Arabidopsis* nucleotide sequence rsw2 (genomic; Accession number At5g4970).
SEQ ID No. 2: cotton nucleotide sequence rsw2 (cDNA)
SEQ ID No. 3: *Arabidopsis* nucleotide sequence rsw3 (genomic)
SEQ ID No. 4: cotton nucleotide sequence rsw3 (corresponding to the 3' end; cDNA)
SEQ ID No. 5: *Arabidopsis* amino acid sequence rsw2
SEQ ID No. 6: cotton amino acid sequence rsw2
SEQ ID No. 7: *Arabidopsis* amino acid sequence rsw3
SEQ ID No. 8: cotton amino acid sequence rsw3 (partial)
SEQ ID No. 9: *Arabidopsis* nucleotide sequence rsw2 (cDNA)
SEQ ID No. 10: oligonucleotide PCR primer (forward rsw2 cotton)
SEQ ID No. 11: oligonucleotide PCR primer (reverse rsw2 cotton)
SEQ ID No. 12: oligonucleotide PCR primer (forward LFY3)
SEQ ID No. 13: oligonucleotide PCR primer (reverse LFY3)
SEQ ID No. 14: oligonucleotide PCR primer (forward MBK5/α)

SEQ ID No. 15: oligonucleotide PCR primer (reverse MBK5/ α)

SEQ ID No. 16: oligonucleotide PCR primer (At glucosidase II α forward)

SEQ ID No. 17: oligonucleotide PCR primer (At glucosidase II α reverse) 10

SEQ ID No. 18: oligonucleotide PCR primer (At glucosidase II β forward)

SEQ ID No. 19: oligonucleotide PCR primer (At glucosidase II β reverse)

SEQ ID No. 20: oligonucleotide PCR primer (forward primer to isolate genomic copy RSW3)

SEQ ID No. 21: oligonucleotide PCR primer (reverse primer to isolate genomic copy RSW3)

SEQ ID No. 22: oligonucleotide PCR primer (forward RWS3 homologue cotton)

SEQ ID No. 23: oligonucleotide PCR primer (reverse RSW3 homologue cotton).

EXAMPLE 1

Isolation of a Full Length cDNA of the GhKOR Gene (Cotton Gene Corresponding to the rsw2 Mutation in *Arabidopsis*)

Figure 1:
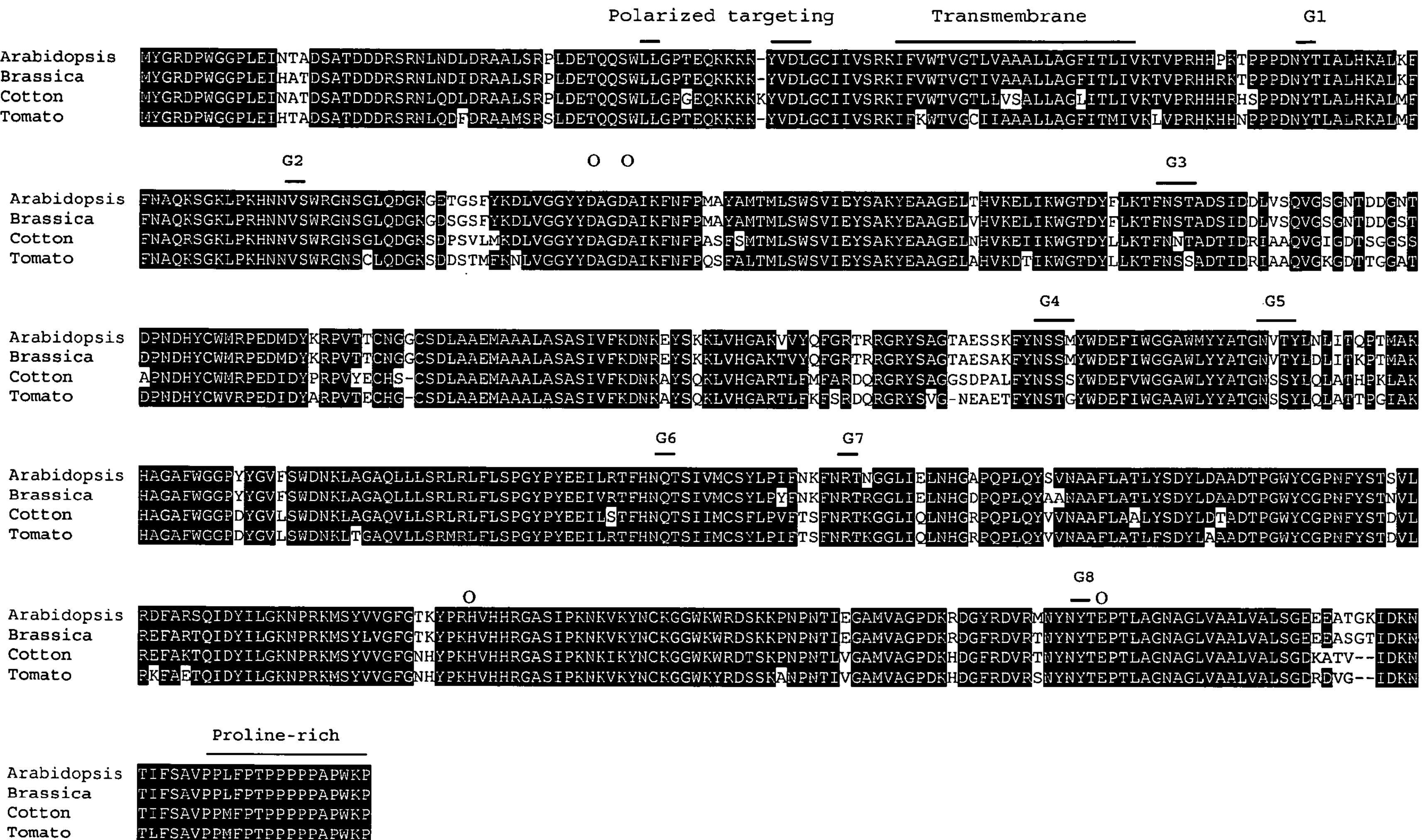
FIG. 1. ClustalW alignment of proteins GhKOR (SEQ ID No 6), and LeCel3 (Accession number T07612; SEQ ID No 24) and AtKOR1 (Accession number At5g49720; SEQ ID No 5) and BnCel16 (Accession number CAB51903; SEQ ID No 25). Features highlighted are: polarized targeting motifs implicated in targeting to the cell plate (Zuo et al., 2000); a putative transmembrane region near the N-terminus (transmembrane); four of the conserved residues potentially involved in catalysis (Asp-198, Asp-201, His-516 and E-555; labeled o) and representing part of the strong similarity to family 9 glycoside hydrolases; a C-terminal region rich in Pro and characteristic of membrane-bound members of the endo-1,4-β-glucanase family; 8 putative N-glycosylation sites (Asn-X-Ser/Thr; labelled G1 to 8).

The NCBI EST database has 7 ESTs from a *Gossypium arboreum* 7-10 dpa (days post anthesis) fiber library which show similarities to the sequence of AtKOR1. The sequences of five of the seven ESTs were identical. Alignment of the three different cotton ESTs against the AtKOR1 cDNA showed that cotton clone AW726657 contained the ATG start codon, and 47 bp of 5' untranslated region. Clone BE052640 spanned the middle region of the KOR gene and overlapped clone AW668085 which contained a TGA stop codon in the same position as that in AtKOR1 and 126 bp of 3' untranslated sequence. Translation of the ORF showed >80% amino acid sequence identity to regions of AtKOR1 protein. Primers designed to the 5' and 3' untranslated regions of the *G. arboreum* ESTs were used to amplify a 1.9 kb PCR product from an 18 dpa fiber cDNA library from the *G. hirsutum* cultivar Siokra 1-4. The forward primer was 5'-CCGCTC-GAGCGGGCATTTTCCGCCCACTA-3' (SEQ ID No. 10) and the reverse primer 5'-CGGGATCCCGTCACACATG-GACAGAAGAA-3' (SEQ ID No 11). A full length cDNA of the cotton KOR gene was generated by the PCR of a cotton cDNA library from 18 dpa fibers of *Gossypium hirsutum* and the products of several amplifications sequenced (SEQ ID No. 2). The cDNA encoded a protein (GhKOR) of 619 amino acids (SEQ ID No. 6) that was highly similar to LeCel3 (86% amino acid identity), AtKOR1 (82% amino acid identity) and BnCel16 (82% identity) (FIG. 1). All proteins shared: polarized targeting motifs involved in targeting AtKOR1 to the cell plate (Zuo et al., 2000); a putative transmembrane region near the N-terminus; four of the conserved residues potentially involved in catalysis (Asp-198, Asp-201, His-516 and E-555; Nicol et al., 1998) as part of the strong similarity to family 9 glycoside hydrolases; a C-terminal region rich in Pro and characteristic of membrane-bound members of the endo-1,4-β-D-glucanase family; 8 putative N-glycosylation sites (Asn-X-Ser/Thr) in the N-terminal domain predicted to be in the ER lumen during glycosylation. (An additional site present only in GhKOR (residues 14-16) would face the cytosol).

EXAMPLE 2

Complementation of the *Arabidopsis* rsw2-1 Mutant with GhKOR

The cotton PCR product encoding GhKOR was cloned behind the CaMV 35S promoter in the following way: the forward primer incorporated a XhoI site (underlined), and the reverse primer a BamHI site (underlined) which allowed the amplified 1.9 kb fragment to be ligated into the appropriate sites in vector pART7 (Gleave, 1992). This placed the cDNA in the sense orientation behind the cauliflower mosaic virus 35S promoter. The complete expression cassette was removed by digestion with NotI and cloned into the corresponding site in the binary vector pART27. The amplified product was sequenced to confirm its identity. This construct was introduced into *Agrobacterium tumefaciens* strain AGL1 and used to transform the rsw2-1 mutant and wild-type Columbia by floral dipping (Clough and Bent, 1998).

Kanamycin resistant transformants were selected on Hoagland's plates containing kanamycin (50 μg/ml) and timentin (100 μg/ml), transferred to vertical Hoagland's plates without selection agents and screened for root swelling after 2 days at 29° C. T2 seed was collected from ten individual T1 plants showing a wild-type phenotype and checked for inheritance of the complemented phenotype in the T2 generation. Photographs were taken of roots of T3 seedlings that were homozygous for kanamycin resistance and had been exposed to 29° C. for 2 d. Other plants grown in pots at 21° C. until the bolt was initiated had the bolt cut off before transfer to 29° C. and the regenerated secondary bolts were photographed when mature. rsw2-1 has a single nucleotide change from Columbia in At5g49720 that replaces Gly-429 with Arg in AtKOR1 and provides a temperature-sensitive phenotype (Baskin et al.,1992; Lane et al., 2001). Plants were grown either in pots (1:1:1 mix of peat:compost:sand), or aseptically in Petri dishes (MS or Hoagland's medium with agar) (Burn et al., 2002a). Growth cabinets provided 100 μmol $m^{-2}$ $s^{-1}$ of continuous light at 21° C. unless otherwise stated. Roots of the rsw2 mutant show temperature-sensitive radial swelling (Baskin et al., 1992) and stems show temperature-sensitive inhibition of elongation (Lane et al., 2001).

Figure 2:
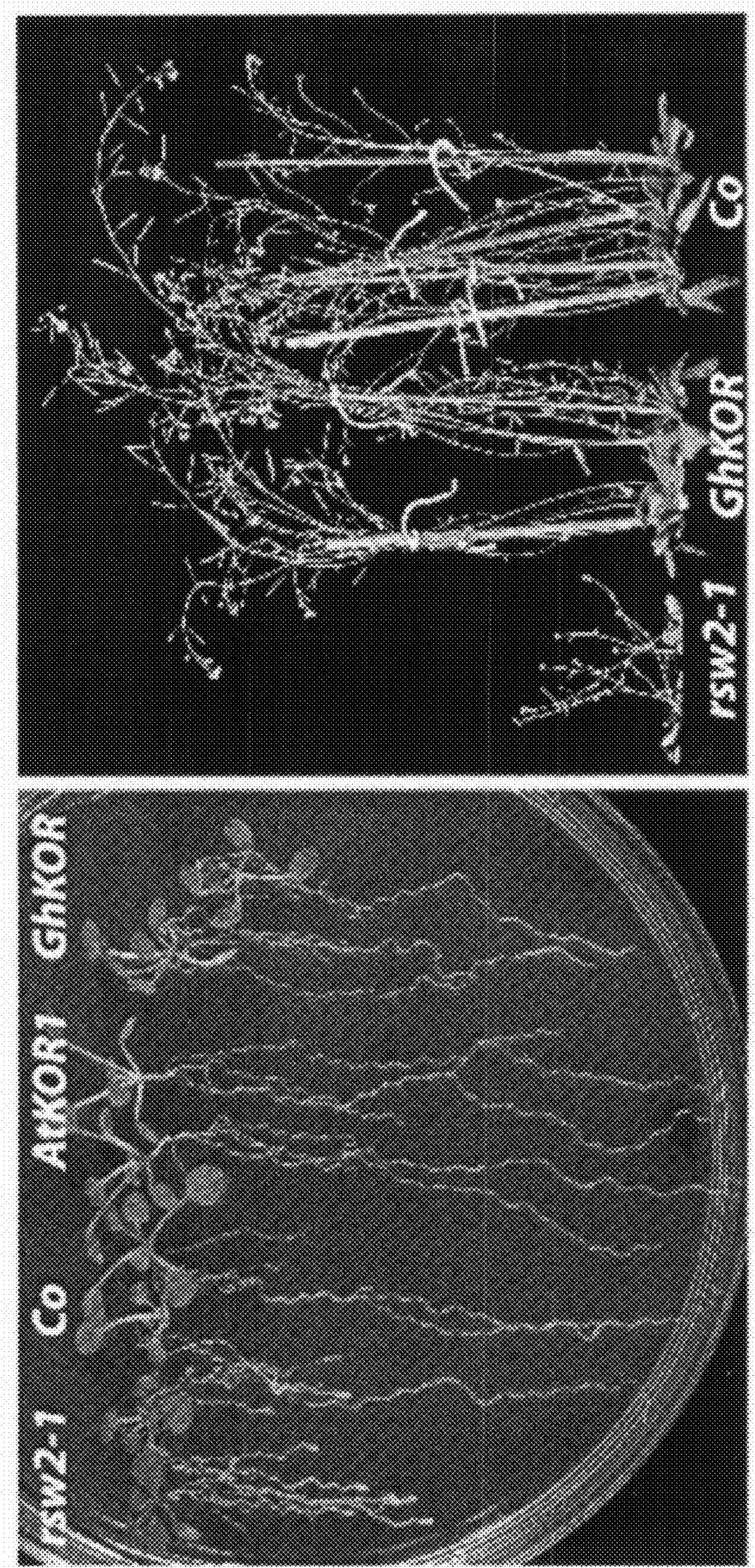
FIG. 2. Complementation of rsw2-1 by transformation with GhKOR1 cDNA (SEQ ID No 2), operably linked to the CaMV35S promoter. (A) Roots of rsw2-1 swell after exposure to 29° C. for 2 d but wild type (Co) and complemented plants containing either AtKOR1 or GhKOR do not. (B) Mature stems of two plants each of rsw2-1 (left), wild type and rsw2-1 expressing GhKOR. Photograph of plants grown in pots at 21° C., until bolting began, at which time bolts were cut off and plants transferred to 29° C. for bolts to regrow.

The roots of 63 out of 75 of the kanamycin-resistant T1 seedlings did not swell after 2 d at 29° C. The wild type phenotype was stably inherited into the T3 generation and roots (FIG. 2A) and stems (FIG. 2B) elongated normally at the restrictive temperature. Stem growth in T3 plants homozygous for kanamycin resistance was quantitatively indistinguishable from wild type. A gene was thus identified encoding a cotton homologue of AtKOR1 and it was shown that it can functionally replace the *Arabidopsis* gene in the rsw2-1 cellulose synthesis mutant.

This will involve GhKOR correcting defects in cytokinesis and cell elongation in *Arabidopsis* (Nicol et al., 1998; Zuo et al., 2000; Lane et al., 2001; Sato et al., 2001) as well as proper interaction with other elements of the cellulose synthesis machinery and/or products. Previous studies identified a cotton fiber protein immunologically related to LeCel3 (Peng et al., 2001) and indirect evidence implicated it in cellulose synthesis in vitro by cotton fiber membranes (Peng et al., 2002). The similarities to LeCel3, BnCel16 and AtKOR1 includes all major features of known functional significance and those, such as the Pro-rich C-terminus, which have no currently known function. The role of an endo-1,4-β-D-glucanase in cellulose synthesis is not clearly established but could involve severing a yet-to-crystallize glucan from a lipid-linked primer or donor (Williamson et al., 2001; Peng et al., 2002).

EXAMPLE 3

Identification and Isolation of the Gene that has been Mutated in rsw3 Mutant of *Arabidopsis thaliana*

The rsw3 allele behaves as a single Mendelian recessive locus (Baskin et al, 1992) and was identified by a map based strategy. The F2 progeny from crossing rsw3 with the visual marker line W9 linked RSW3 with yi on the lower arm of chromosome 5. An F2 population from crossing rsw3 (Columbia background) with the Landsberg erecta ecotype was screened to give plants showing a root swelling phenotype. DNA was prepared from 2-3 rosette leaves per plant using the FastDNA kit (BIO 101, Carlsbad, Calif.) and mapping carried out using LFY3 (forward primer 5'-GACGGCGTCTAGAAGATTC-3' (SEQ ID No. 12), reverse 5'-TAACTTATCGGGCTTCTGC-3'; SEQ ID No. 13; cleavage with RsaI) and MBK5/α (forward 5'-CCCTCGCTTGGTACAAGGTAT-3' (SEQ ID No. 14) and reverse 5'-TCCTGATCCTCTCACCACGTA-3' (SEQ ID No. 15). Using the F2 from a cross to the Landsberg erecta ecotype, RSW3 was mapped at 6 cM from the LFY3 locus (4 out of 70 chromosomes showing a cross over event) so positioning RSW3 between yi and LFY3. Analysis of a further 372 chromosomes identified one recombination event between MBK5/α and rsw3, a notional map distance of 0.27 cM. Several candidate genes in this region were sequenced in rsw3. One (At5g63840) on the P1 clone mgil9 (AB007646) encoded a putative catalytic subunit of glucosidase II and the rsw3 allele showed a T to C substitution predicted to replace Ser599 with Phe in the protein (nucleotide sequence of the wild type RSW3 gene is represented in SEQ ID No. 3, amino acid sequence of the encoded protein is represented in SEQ ID No. 7).

The RSW3 sequence is highly similar from about residue 150 onwards to sequences in the glucoside hydrolase family 31 (Henrissat, 1991; Henrissat and Bairoch, 1993). Monroe et al identified the RSW3 glucosidase II gene through a search of *Arabidopsis* ESTs with homology to α-glucosidases and named it Aglu-3 (Monroe et al., 1999). Its protein product formed a clade with several glucosidase II enzymes whose catalytic activities were independently known. They all separated from apoplastic α-glycosidases of *Arabidopsis* with which Aglu-3/RSW3 shares only 8% sequence identity. FIG. 4 shows the two signature motifs for the clade containing Aglu3/RSW3, which are believed to include catalytic and substrate binding residues. Aglu3/RSW3 contains all of the conserved residues within these motifs, as well as the proposed catalytic residues Asp512 and Asp617 (Frandsen and Svensson, 1998). Ser599, which is mutated in rsw3, is likely to be functionally significant since it is conserved in the homologous gene product from mouse (NP 032086), human (NP 055425), pig (AAB49757), slime mold (AAB18921), potato (P07391) and cotton (see below), and in the more distantly related apoplastic α-glucosidases encoded by the *Arabidopsis* genes Aglu-1 and Aglu-2 (Monroe et al., 1999). The *Arabidopsis* Aglu-3/RSW3 gene appears to be a single copy, spans 3.84 kb with 5 introns and encodes a predicted transcript of 2766 bp giving a predicted translation product of 104 kDa.

Recent biochemical (Trombetta et al, 1996) and genetic studies (D'Alessio et al, 1999; Pelletier et al., 2000) suggest that native glucosidase II of mammals and yeast consists of a catalytic α-chain (to which Aglu-3/RSW3 is homologous) and a smaller non-catalytic β-chain which retains the heterodimer in the ER. To determine if *Arabidopsis* contained an ortholog of the β-subunit, a BLAST search of the NCBI database was carried out with the mouse β-subunit. Unknown protein At5g56360 (protein MCD7.9 on the P1 clone MCD7 (AB009049) from chromosome 5) had 27% amino acid identity and 42% similarity to the mouse β-subunit. A closely related sequence (GenbankBAA88186) exists on chromosome 1 in rice but is annotated with a stop codon that truncates it after 496 residues. The conceptual translation of the adjacent 3' sequence on the PAC clone P0038F12 (AP000836) and reconsideration of proposed splice sites indicate the potential to encode a full length β-subunit that is very similar to the *Arabidopsis* gene product. The proposed sequence of the gene product is supported by an EST (AU030896) matching the proposed exons. FIG. 5 therefore includes our suggestion for the full length rice protein. The *Arabidopsis*, rice, mouse and *Schizosaccharomyces pombe* sequences share: HDEL ER-retention signals at the C-termini; predicted leader sequences at their N-termini; a cysteine-rich N-terminal region; a MHR (mannose-receptor homology region) (Munro, 2001) preceding the HDEL sequence at the C-terminus; a central region rich in acidic residues and flanked by regions giving high scores in programs ("Coils" and "Paircoil") predicting the likelihood of sequences forming coiled coils (Berger et al., 1995; Lupas et al, 1991).

Munro (2001) links the MRH domain to carbohydrate recognition. It comprises a region of similarity to the cation-dependent mannose 6-phosphate receptor whose crystal structure is known. Critical conserved features (FIG. 5) include the 6 Cys residues forming 3 disulphide bonds (although the *S. pombe* protein lacks cysteines 1 and 2), the substrate recognition loop between the cysteines 5 and 6 and the Y and R residues implicated in ligand binding (Roberts et al., 1998). Interaction between mouse α and β subunits was mapped to the N-terminal 118 residues of the β-subunit, which are reasonably well conserved in all sequences, and to residues 273-400 (Arendt and Ostergaard, 2000) which are not. FIG. 5 shows, however, that all sequences show a high percentage of acidic residues.

Expression of the genes encoding the α and β-subunits was analyzed using RT-PCR in the following way. RNA (Parcy et al., 1994) was treated with RQ1 RNase-free DNase (Promega, Madison, Wis.) following the manufacturer's instructions. PCR primers were designed to the 3' end of the coding region of the α and β-subunits of *Arabidopsis* glucosidase II:

```
α-forward
5'-CGTAGTGGTCTACTGGTTCAA-3',  (SEQ ID No 16)

α-reverse
5'-TGAGCTGTGTCCCAAGAGGAT-3',  (SEQ ID No. 17)

β-forward
5'-GGTGATGAGGATACCAGCGAT-3',  (SEQ ID No. 18)

β-reverse
5'-CCCACTCCCTAACCGGAGTTT-3',  (SEQ ID No. 19)
```

Each primer spanned an intron so differentiating RT-PCR products from genomic DNA and mRNA (724 bp versus 452 bp for the α-subunit, 996 versus 474 for the β-subunit). RT-PCR was carried out using the Gibco BRL Superscript one step RT-PCR kit, following the manufacturer's instructions and an RT-PCR cycle of 48° C. 45 min, 94° C. 2 min, (94°

Figure 6:
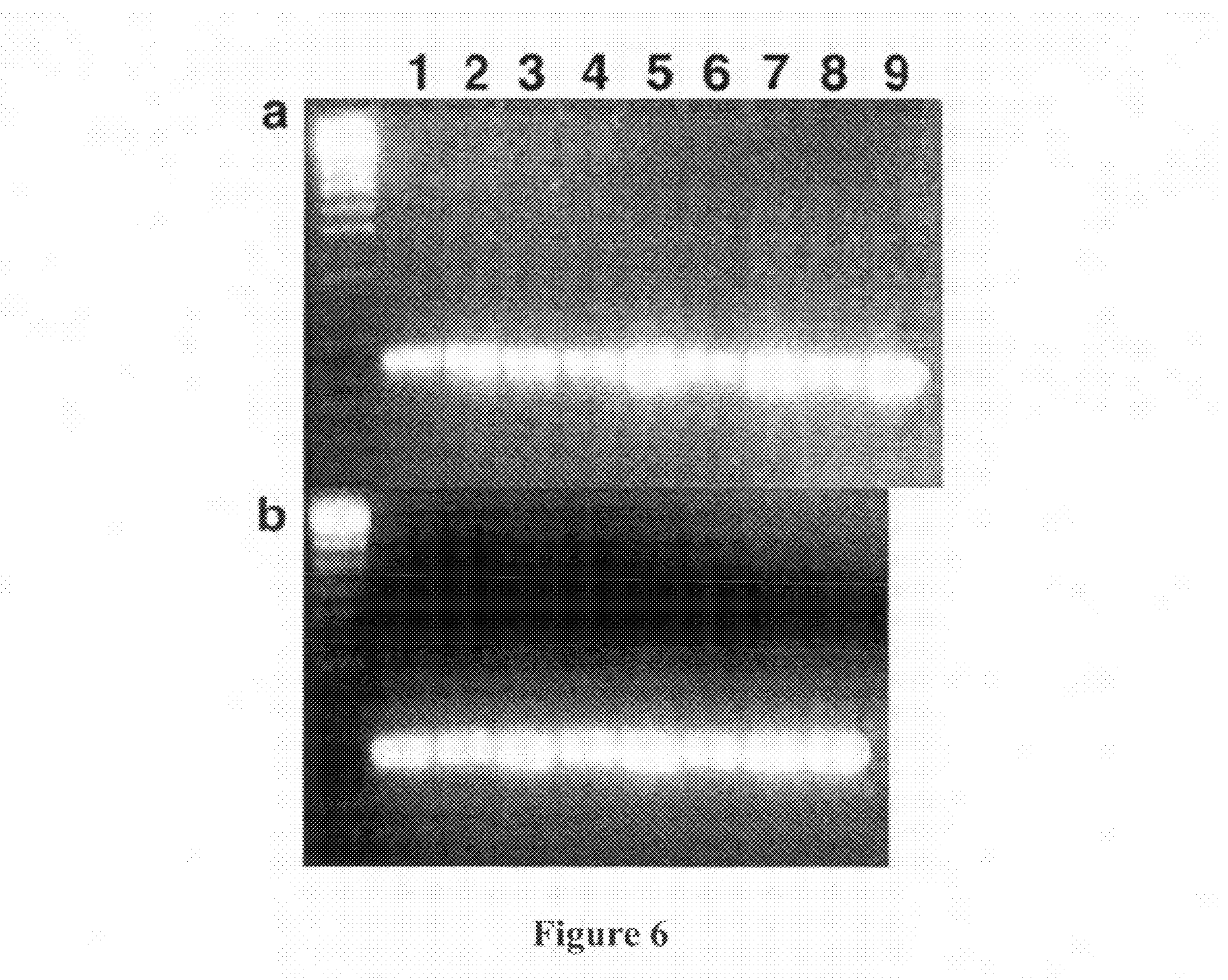
FIG. 6. mRNA for both the α-subunit (a) and the β-subunit (b) occurs in all *Arabidopsis* tissues tested. RT-PCR using mRNA from root (lane 1), whole rosette leaves (2), leaf blades (3), mature stem tissue (4), cauline leaves (5), flower buds (6), flowers (7), siliques (8), dark grown hypocotyls (9). (The presence of the β-subunit in dark grown hypocotyls was demonstrated in another experiment).

C./30 sec, 54° C./1 min, 68° C./2 min)×45, 72° C. –7 min. RT-PCR detected expression of the genes encoding the α and β-s in all tested tissues of *Arabidopsis* (FIG. 6) but, under the conditions used, will not clearly indicate relative expression levels. The low numbers of ESTs in *Arabidopsis* (13 for the α-subunit, 4 for the β-subunit), suggest neither gene is highly expressed. (For comparison, AtCesA1/RSW1, a glycosyltransferase implicated in cellulose synthesis, detects 40 ESTs in a similar search.)

EXAMPLE 4

Figure 3:
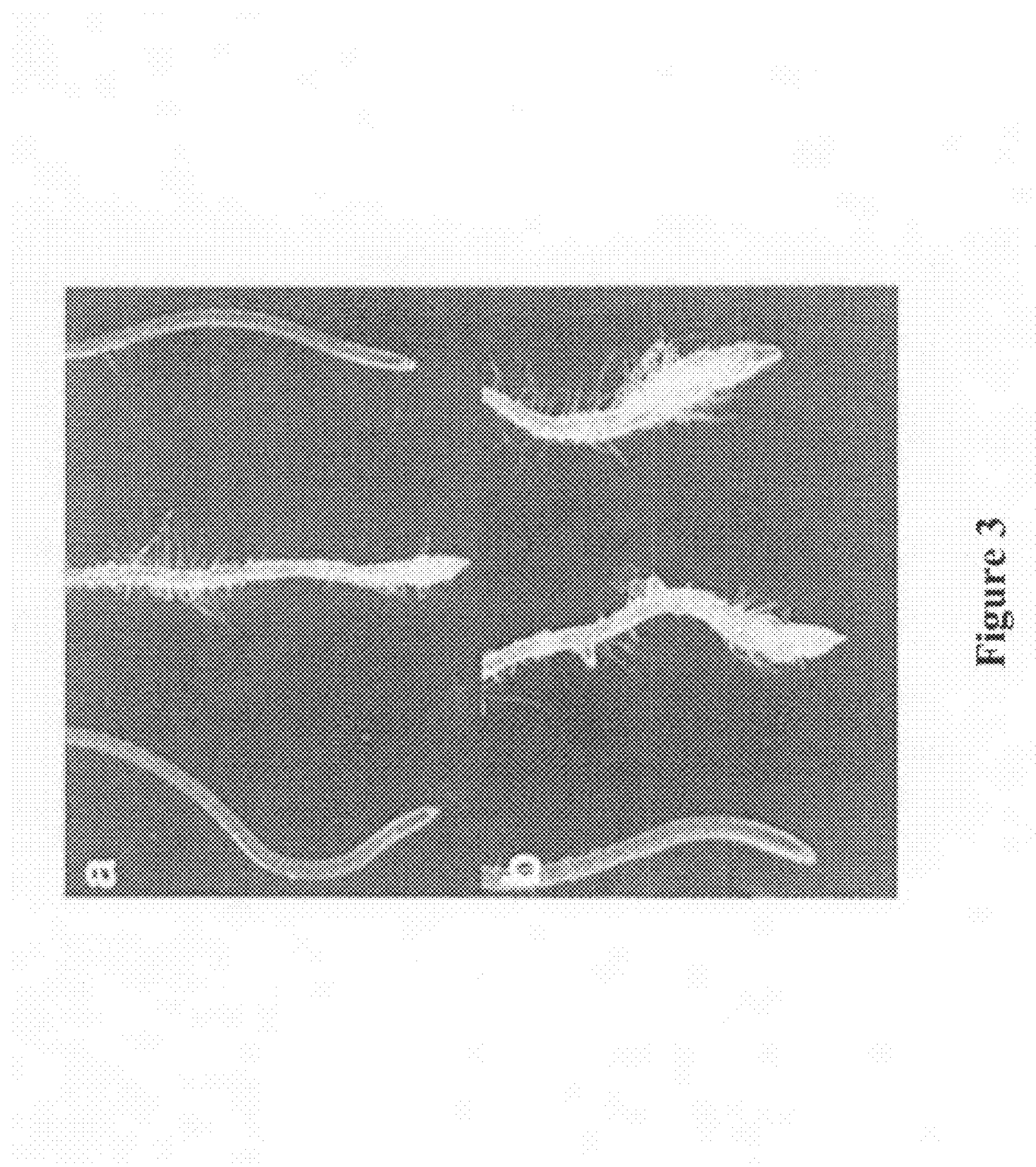
FIG. 3. Mutations in the gene encoding glucosidase II cause radial swelling. (a) Complementation of root radial swelling in rsw3 transformed with the 5.8 kB fragment amplified from the wild-type genome. Columbia wild type (left), rsw3 (center) and a kanamycin-resistant T1 seedling of rsw3 transformed with a genomic copy of the glucosidase II gene (right). The wild type gene suppresses radial swelling. All plants were transferred to 30° C. for 2 d prior to photographing. (b) The rsw3 mutation is allelic to the insertional mutant 5GT5691 which contains a Ds element in the first exon of the glucosidase II gene. Columbia wild type (left), rsw3 (center) and a heterozygous F1 plant from crossing 5GT5691 with rsw3. The F1 heterozygote and the rsw3 homozygote show temperature-induced radial swelling. All plants were transferred to 30° C. for 2 d prior to photographing.

Complementation of the rsw3 Mutation by a Genomic Copy of the *Arabidopsis* Gene A genomic copy of the glucosidase II α-subunit including 830 bp of the promoter region was generated by PCR amplification of BAC F20A11 using the forward primer 5'-CCGCTCGAGCGGTTTCACTCACAACT-GTGGTCTCT-3' (SEQ ID No. 20) and the reverse (SEQ ID No. 20) and the reverse primer 5'-CCGCTCGAGCG-GTCTCCTAAGTCCTAACCCCATA-3' (SEQ ID No. 21). Both primers included a XhoI site (underlined) which allowed the amplified 5.8 kb fragment to be ligated into the SalI site in the binary vector pBin19. The amplified product showed a single base pair change (C to T) from the genomic sequence. This substituted Leu for Ser 142, a residue that is conserved in potato but not in other species (FIG. 4) and did not impair the ability of the fragment to complement rsw3. The construct was introduced into *Agrobacterium tumefaciens* strain AGL1 and used to transform the rsw3 mutant by floral dipping (Clough and Bent, 1998). Kanamycin-resistant transformants were selected at 21° C. on Hoaglands's plates containing kanamycin (50 μg ml$^{-1}$) and timentin (100 μg ml$^{-1}$). Healthy seedlings were transferred to vertical Hoagland's plates and placed at 30° C. for 2 days to screen for root swelling. Kanamycin resistant T1 progeny had wild-type roots when grown for 5 days at 21° C. followed by 2 days at 30° C. (FIG. 3*a*). The inflorescence phenotype (see later) was also complemented.

A second line of evidence was provided by crosses between rsw3 and the tagged mutant SGT5691 (Parinov et al., 1999), which contains a Ds element in the first exon of the gene encoding the putative glycosidase II enzyme. It presumably represents a null allele and the mutation is homozygous lethal so hemizygous plants, which appear wild type, were used for crossing. The NPTII gene present on the Ds element confers kanamycin resistance to F1 plants receiving the tagged allele from SGT5691. Roots of all kanamycin-resistant F1 seedlings (containing a null allele and a temperature-sensitive allele) appeared wild-type at 21° C. but swelled at 30° C. (FIG. 3*b*). This confirms that the Ds insertion mutant and the EMS generated mutant rsw3 are allelic and that glucosidase II defects cause radial swelling.

EXAMPLE 5

Figure 7:
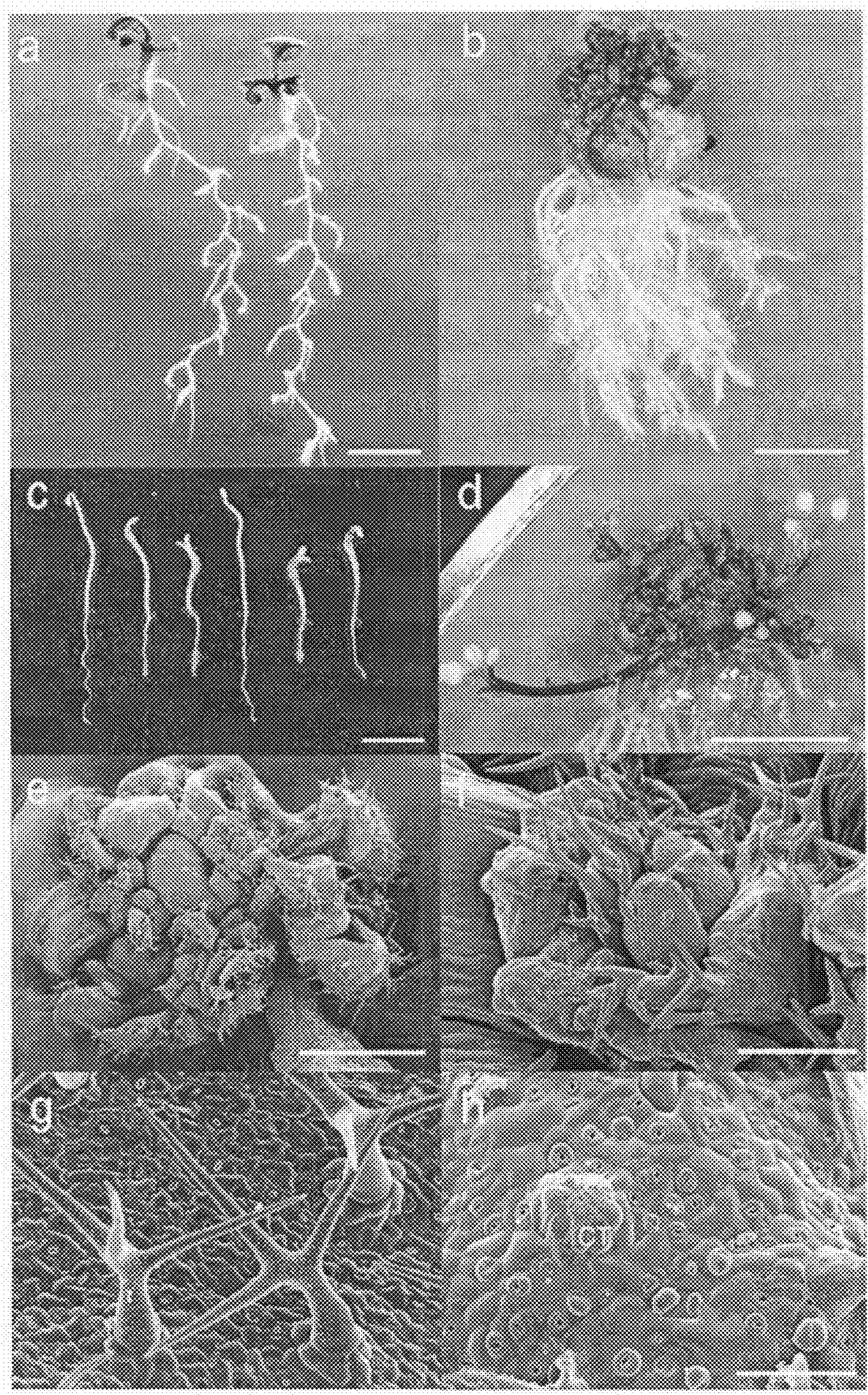
FIG. 7. Morphology of rsw3.

Observations on Other Phenotypes Associated with the rsw3 Mutation in *Arabidopsis* rsw3 grows like wild type at its permissive temperature of 21° C. and the seedling root swells when transferred to 30° C. The bulging cells on the root (Baskin et al., 1992) are often at the base of root hairs suggesting a role for RSW3 in the early stages of root-hair development. The swollen primary root only resumes elongation if returned to the permissive temperature within 48 h but the root continues to generate laterals (FIG. 7*a*). The laterals—whose primordia were not visible when the transfer to 31° C. was made—elongate for several mm before they in turn swell and stop growing. The root system of mature vegetative plants is consequently short and very highly branched (FIG. 7*b*). The double cellulose-defective mutant rsw1-rsw3 showed only a slightly swollen root tip after 24 h at the restrictive temperature but since any longer period at the high temperature led to death, swelling was probably already curtailed after 24 hours at the restrictive temperature.

The phenotype in dark-grown hypocotyls is much weaker in rsw3 than in rsw1-1 and rsw2-1 and the phenotype in rsw1-1rsw3 is weaker than rsw1-1rsw2-1 (FIG. 7*c*). Roset growth of rsw3 in the light is strongly suppressed and many minute leaves are packed in a dense mat in which regular phyllotaxis cannot be recognized (FIG. 7*d-f*). The complex pavement cell shape in wild-type leaves (FIG. 7*g*) is simplified in rsw3, stomata protrude from the leaf surface and some trichomes appear to burst (FIG. 5*h*). Several of the crowded rosettes initiated minute inflorescences (FIG. 7*d*) although these appear much later than wild-type inflorescences (28.6±0.5 days versus 15.5±0.17 days for agar grown plants; mean±SE, n=98 for rsw3, n=45 for wild type). The few flowers on the minute rsw3 inflorescences were essentially full-sized although anther filaments, gynoecium and sepals were slightly shortened and buds opened prematurely before the stigma was receptive (similar to the buds from soil grown rsw3 plants shown in FIG. 8*e, f* which are discussed below).

To investigate the direct effects of the mutation on stem growth, wild-type and rsw3 were grown at 21° C. on soil so that subsequent inflorescence development would not be limited by a small rosette supplying little photosynthate. Rosettes of rsw3 were very similar to wild type under these conditions and reproductive growth began at the normal time.

Primary bolts were cut off and regrowth of secondary bolts followed at either 21° C. or 30° C. (FIG. 6*a, b*). Regrowth followed a slightly S-shaped curve with rsw3 and rsw1-1 at 21° C. showing statistically insignificant reductions in growth rate and final height relative to wild type. Rsw1-1rsw3 showed a clear reduction in rate and final height. At 30° C., however, the rsw3 growth rate was similar to wild type for a few days but elongation stopped by about day 5 whereas it continued in wild type until day 16 and even longer in rsw1-1 (FIG. 8*b*). rsw1-1rsw2 (Lane et al., 2001) failed to regenerate secondary bolts at 30° C. and rsw1-1rsw3 only grew to about 35 mm (FIG. 8*b*) and produced few flowers and no seed.

Measurements of daily stem growth increments and the lengths of epidermal cells, which had left the elongation zone when the bolts were about half grown (Table 1), were made. This allowed estimation of cell flux (the number of cells leaving the elongation zone day$^{-1}$) at that time since daily growth increment=cell length×cell flux. There was no significant reduction in either cell flux or cell length of rsw3 growing at 21° C. The rsw1-1rsw3 constitutive phenotype at 21° C. was entirely due to a reduction in cell length. At 30° C., rsw1-1 showed a 57% reduction in cell length and a 35% reduction in cell flux relative to wild type.

Analyses of this type require that the plant is in a near steady state with respect to growth rate, length of the elongation zone etc. Conditions, however, are far from steady state when elongation is rapidly slowing in rsw3 and rsw1-1rsw3 so that accurate deductions of cell flux for those genotypes are precluded. To get at least an idea of how cell length was behaving when growth was slowing, we measured cell lengths at a height of about 80 mm on the rsw3 stem. (FIG. 8*b* shows that when these cells left the elongation zone, the stem would have been near the end of its growth phase since total plant height at that time would have exceeded 80 mm by the length of the growth zone at that time; 40 mm in wild type according to Fukaki et al., 1996). The cells in rsw3 were, even then, only slightly shorter than wild type (Table 1) suggesting that falling cell production rates were probably more important than reduced cell expansion in slowing stem elongation. In contrast, when we sampled the rsw1-1rsw3 stem at 30 mm for cells maturing when its elongation was slowing (FIG. 8*b*), cell length was reduced by 57% (Table 1). This is consistent with the presence of rsw1-1 in the double mutant tilting the balance strongly towards reduced cell length.

These conclusions regarding cell division and cell expansion were checked in a simpler system by using cryo-scanning electron microscopy to examine stamen filaments in flowers showing receptive stigmas (Table 2). The results were similar: rsw3 plants again showed a greater percentage reduction in cell number than in cell length and the double mutant rsw1-1rsw3 showed a further reduction in cell length without an additional reduction in cell number. Rsw1-1 showed a much greater reduction in cell length than in cell number (Table 2). Stems of both wild type and rsw3 regenerating at 30° C. reached approximately the same height before initiating their first flower even though their final heights would be very different (FIG. 8*b*). Wild-type stems generated about 27 well spaced flowers before elongation ceased but rsw3 produced only about 6 closely spaced flowers before elongation ended leaving a cluster of flowers (FIG. 8*c, d*). rsw3 flower buds opened precociously before the stigma was receptive (FIG. 8*e, f*).

Few flowers and no seed formed on the minute bolts of rsw3 plants grown continuously at their restrictive temperature (FIG. 7*d*). Even flowers on the much larger bolts formed at 31° C. on plants which had completed vegetative growth at 21° C. (FIG. 8*d, f*) also set very little seed. That seed (FIG. 8*g, h*) was shrunken (probably because of reduced accumulation of seed storage proteins; Boisson et al., 2001), its surface lacked the regular cellular structure of wild type grown at 30° C. or of rsw3 grown at 21° C. and it showed very little secreted mucilage after imbibition (FIG. 8*i-n*). Reduced mucilage secretion was not typical of cellulose-deficient mutants: rsw1-1 (defective in the CesA1glycosyltransferase; FIG. 8 *k, l*), and rsw2-1 (defective in the KOR endo-1,4 β glucanase) had normal mucilage coats.

To isolate effects on the haploid stages of pollen and ovule development from effects on the diploid stages, we examined seed set in the hemizygous Ds-mutant SGT5691 (a presumed null allele in the glucosidase II catalytic subunit). Seed set by self-fertilization segregates 147 kanamycin-resistant individuals to 153 sensitive individuals. A ratio less than the 2:1 expected for a dominant, homozygous lethal allele shows that the null allele affects post-meiotic development of pollen and/or ovules. We separated the effects on the male and female pathways by reciprocal crosses between the hemizygous tagged mutant and Landsberg erecta (the appropriate wild type for this mutant). Kanamycin-resistant and sensitive plants will segregate 1:1 if pollen or ovule development is unaffected with lower ratios if the null allele reduces pollen or ovule fertility. Pollen from the Ds-tagged mutant gave a segregation ratio of 1:16 (6 resistant:94 sensitive individuals) indicating a 94% reduction (relative to wild type) in the ability of Ds-tagged pollen to set viable seed. This compared with a 41% reduction when Ds-tagged ovules were crossed to wild type pollen (ratio of 1:1.7, 37:63 individuals). The null allele of glucosidase II therefore affects the haploid stages of pollen development much more severely than it affects post-meiotic ovules.

Roots of 7 day old seedlings of rsw3 grown at 31° C. contain only 51% of the wild-type cellulose (expressed mg-1 tissue dry weight), a comparable figure to that resulting from single amino acid substitutions in the CesA1 glycosyltransferase (rsw1-1) and the KOR endo-1,4-β-glucanase (rsw2-1) (Peng et al., 2000). The morphological changes indicate that all three genes are needed to make cellulose in primary cell walls.

Production of Golgi-derived non-cellulosic polysaccharides changes little in rsw3 seedlings (Peng et al., 2000). The selectivity for cellulose production is comparable to that seen with a defect in glucosidase I (Gillmor et al., 2002), the enzyme generating the initial substrate for glucosidase II processing. It exceeds the selectivity seen in the embryo-lethal cyt1 mutants of *Arabidopsis* (defective in mannose-1-phosphate guanylyltransferase) (Lukowitz et al., 2001) and in potatoes with MAL1 (encoding a glucosidase II α-subunit) down-regulated by antisense (Taylor et al., 2000a) where complex changes occur in non-cellulosic polysaccharides and lignin. We therefore conclude that cellulose synthesis is often much more sensitive to N-glycan processing defects than is the synthesis of non-cellulosic polysaccharides in the Golgi.

Secretion of Golgi-derived seed mucilage is strongly reduced in rsw3 but not in rsw1-1 or rsw2-1. Mucilage could be produced but retained intracellularly (perhaps because of structural changes resulting from cellulose deficiency), or mucilage production itself could be reduced. Many developmental blocks reduce mucilage production (Western et al., 2001; Western et al., 2000) but we cannot yet exclude the possibility that rsw3 has defective processing of Golgi enzymes required to make the particular non-cellulosic polysaccharides making up the mucilage.

Cell numbers and sizes in stamen filaments indicate that rsw3 affects cell division more strongly than cell expansion. The cell length data for the stem are consistent with this finding. A strong effect of rsw3 on cell division may explain why its phenotype is rather weak in dark grown hypocotyls which lack cell division (Gendreau et al., 1997). In more strongly affecting cell division than cell expansion, rsw3 resembles rsw2-1 (Burn et al, 2002) rather than rsw1-1 (Burn et al., 2002) or plants carrying antisense constructs to RSW1/CesA1 or CesA3 (Burn et al., 2002) which are more severely affected in cell length. (Although CesA1 changes have little impact on division rates, CesA1 is probably expressed in dividing root cells since they show changes in wall ultrastructure (Sugimoto et al., 2001) and swell (Baskin et al., 1992; Beemster and Baskin, 1998) when rsw1-1 is at its restrictive temperature.)

Although it is clear that cellulose biosynthesis is impaired in the rsw3, the mechanism by which rsw3 affects cellulose synthesis is not yet clear. As noted in relation to a glucosidase I mutation (Boisson et al., 2001), the minimal phenotype shown by a mutant which cannot assemble mature N-linked glycans in the Golgi (von Schaewen etal, 1993) indicates that a lack of mature N-linked glycans on critical proteins will not cause the strong phenotype seen with a glycosidase II defect. Reduced rates of production of Glc1Man9GlcNAc2 and Man9GlcNAc2 would probably slow both the formation and dissociation of the glycoprotein/chaperone complex creating a bottleneck that may in time reduce the steady state levels of glycoproteins at sites further along the secretory pathway. Because glycoproteins participate in many plant processes, it is not obvious why cellulose synthesis should be much more sensitive to processing defects in the ER than, for example, synthesis of non-cellulosic polysaccharides.

Gillmor et al. (2002) argued that CesA proteins are not glycosylated when they did not detect a mobility shift on SDS-PAGE in knopf (deficient in glucosidase I) or alter N-glycosidase F treatment and when they did not see in knopf a change in CesA abundance that was visible by unquantified immunostaining. The KOR endo-1,4-β-glucanase is a better candidate. A soluble fragment of the *Brassica napus* ortholog of KOR is heavily N-glycosylated when expressed heterologously in *Pichia pastoris* and the N-glycan is required for in vitro activity (Molhoj et al., 2001). Further evidence consistent with KOR being a target can be drawn from the rsw3 and rsw2-1 phenotypes affecting cell division more than cell expansion whereas the rsw1-1 phenotype shows the reverse.

The rsw1-1 and rsw2-1 mutations affect genes encoding plasma membrane enzymes that are probably directly involved in cellulose synthesis so that changed enzyme performance at the restrictive temperature will rapidly impact on cellulose synthesis. rsw3, in contrast, encodes a processing enzyme in the ER whose changed performance will reduce cellulose synthesis only when it restricts the supply of properly folded glycoproteins to the site of cellulose synthesis. The different time courses for the onset of a visible phenotype when the three mutants are transferred to the higher temperature plausibly reflect these different modes of action. Radial swelling starts slowly in rsw3 (latency>24 h compared to <12 h in rsw1-1 and rsw2-1) and the high temperature actually accelerates root elongation during the first 12 h, albeit by less than in wild type (Baskin et al., 1992).

Elongation of rsw1-1 or rsw2-1, in contrast, falls during the first 12 h, roots swell strongly and rsw1-1 shows changed wall ultrastructure within 4 h (Sugimoto et al., 2001).

It has been shown that rsw3 is mutated in a gene encoding a putative glycosidase II α-subunit, identified a putative β-subunit encoded by two plant genomes and shown that many aspects of the rsw3 phenotype flow from reduced cellulose synthesis in primary walls. Cell division seems more strongly affected than cell expansion indicating that the KOR endo-1,4-β-glucanase, where mutations also strongly affect cell division, may be the glycoprotein affected by the processing defect. In addition to its role in cellulose synthesis, a temperature-sensitive allele of glucosidase II will contribute to studies of N-glycosylation and quality control in the ER and in establishing its links to other developmental and physiological processes.

EXAMPLE 6

Isolation of a (Partial) cDNA Corresponding to RSW3 from Cotton

A dbEST search using the sequence of RSW3 as query, identified a *Gossypium arboreum* cDNA with 833 bp of high quality sequence. Primers designed from the EST were used to amplify a 700 bp product form a library of 18 dpa fibers of *G. hirsutum* cDNA using the following primers:

```
Cot-rsw3f
5'-CGGGATGAAGAGGATGTAGAG 3'    (SEQ ID No. 22)

Cot-rsq3r
5'-GAACCCCTGAGATGATCCCAA 3'    (SEQ ID No. 23)
```

The PCR product was used as a probe to identify longer cDNAs. 5 putative clones were identified and 2 were sequenced. The three clones overlapped and the sequence of cDNA of the cotton RSW3 homolog was assembled (SEQ ID No. 4). The region encoding the N-terminus is missing.

EXAMPLE 7

Expression of RSW2/RSW3 Chimeric Genes in Cotton cDNAs corresponding to RSW2 or RSW3, isolated from *Arabidopsis* or cotton are operably linked to a promoter such as the expansin promoter and a 3' end region involved in transcription termination and polyadenylation.

Further, about 100 bp long fragments selected from the RSW2 or RSW3 genes isolated from *Arabidopsis* or cotton are cloned in inverted repeat under the control of a promoter such as the CaMV35S promoter.

The chimeric genes are introduced into a T-DNA vector comprising further a selectable marker gene, and the resulting T-DNA vectors are introduced into *Agrobacterium tumefaciens* strains containing a helper Ti-plasmid. Transgenic cotton plants are obtained using these *Agrobacterium* strains.

Plants expressing copies of the different transgenes are analyzed further for cell wall components, including cellulose, non-crystalline β-1,4 glucan polymer, starch and carbohydrate content as described in WO 98/00549.

TABLE 1

Analysis of the rate of stem elongation in terms of cell length and, where near steady growth rates occurred, cell flux (number of cells day$^{-1}$ leaving the elongation zone).

| | | Growth rate (mm day$_{-1}$) | Cell flux (day$_{-1}$) | Cell length (μm) |
|---|---|---|---|---|
| 21° C. | Columbia | 38.7 ± 1.0 | 101 ± 3.5 | 384 ± 4.0 |
| | rsw3 | 38.4 ± 1.4 | 95.9 ± 4.6 | 402 ± 7.0 |
| | rsw1 | 38.9 ± 1.6 | 102 ± 6.9 | 382 ± 9.8 |
| | rsw1rsw3 | 30.2 ± 1.9** | 100 ± 7.6 | 299 ± 8.4** |
| 30° C. | Columbia | 53.8 ± 1.2 | 133 ± 2.7 | 404 ± 3.2 |
| | rsw3 | 41.8 ± 3.1** | | 378 ± 22 |
| | rsw1 | 15.2 ± 1.4*** | 87.2 ± 7.0** | 174 ± 5.8*** |
| | rsw1rsw3 | 13.6 ± 1.8*** | | 173 ± 15*** |

Results are given as mean + SE for n = 5. Statistically significant differences from wild type using the Student's T-test are indicated (* = p < 0.05;  = p < 0.01; * = p < 0.001).

TABLE 2

Cell length and number in mature stamen filaments grown at 30° C.

| | Total length (μm) | Cell number | Cell length (μm) |
|---|---|---|---|
| Columbia | 2407_38 | 17.0_1.0 | 152.7_6.2 |
| rsw3 | 1458_52*** | 11.4_0.3*** | 127.0_0.1** |
| rsw1-1 | 1050_57*** | 15.0_0.4 | 72.7_9.8*** |
| rsw1-1rsw3 | 415_41*** | 12.4_0.5*** | 29.4_2.1*** |

Results are given as mean + SE for n > 7. Statistically significant differences from wild type using the Student's T-test are indicated (* = p < 0.05;  = p < 0.01; *p = < 0.001).

REFERENCES

Arioli et al. (1998) *Science* 279: 717-720.

Arendt et al. (2000) *Glycobiology* 10: 487-492.

Baskin et al. *Aust. J. Plant Phys.* 19: 427-437.

Beemster et al. (1998) *Plant Physiol,* 116: 1515-1526.

Berger et al. (1995) *Proc. Nat Acad. Sci. USA* 92: 8259-8263.

Boisson et al. (2001) *EMBO J.,* 20: 1010-1019.

Brada et al. (1984) *Eur. J. Biochem.,* 141: 149-156.

Brummell et al. *Proc. Nat. Acad Sci. USA* 94: 4794-4799.

Burn et al (2002a) *Plant Physiol.* 129: 797-807.

Clough et al. (1998) *Plant J.* 16: 735-743.
D'Alessio et al. (1999) *J. Biol. Chem.*, 274: 25899-25905.
Desprez, et al. (2002) *Plant Physiol.* 128: 482-490.
Fagard et al. (2000) *Plant Cell* 12: 2409-2424.
Frandsen et al. (1998) *Plant Mol. Biol.* 37: 1-13
Fukaki et al. (1996) *Plant Physiol.* 110, 933-943.
Gendreau et al. (1997) *Plant Physiol.*, 114: 295-305.
Gillmor et al. (2002) *J. Cell Biol.* 156: 1003-1013.
Gleave, A. P. (1992) *Plant Mol. Biol.* 20: 1203-1207.
Helenius et al. (2001) *Science* 291: 2364-2369.
Henrissat (1991) *Biochem. J.* 280: 309-316
Henrissat and Bairoch (1993) *Biochem. J.* 293: 781-788.
Hino and Rothman (1985) *Biochemistry* 24: 800-805.
Kimura et al. (1999) *Plant Cell* 11: 2075-2085.
Lane et al. (2001) *Plant Physiol.* 126: 278-288.
Lukowitz et al. (2001) *Proc. Nat. Acad. Sci USA* 98: 2262-2267.
Lupas et al. (2001) *Plant Physiol.* 127: 674-684.
Mølhøj et al. (2001) *Plant Physiol.* 127: 674-684.
Monroe et al. (1999) *Plant Physiol.* 119: 385-397.
Munro (2001) *Curr. Biol.* 11: R499-501.
Murashige and Skoog (1962) *Phys. Plant* 15: 473-497.
Nicol et al. (1998) *EMBO J.* 17: 5563-5576.
Pagant et al. (2002) *Plant Cell* 14: 2001-2013.
Parcy et al. (1994) *Plant Cell* 6: 1567-1582
Parinov et al. (1999) *Plant Cell* 11: 2263-2270.
Pelletier et al. (2000) *Glycobiology* 10: 815-827.
Peng et al. (2000) *Planta* 211: 406-414.
Peng et al. (2002) *Science* 295: 147-150.
Peng et al. (2001) *Plant Physiol.* 126: 981-992.
Roberts et al. (1998) *Cell* 93: 639-648.
Sato et al. (2001) *Plant Cell Physiol* 42: 251-263.
Scheible et al. (2001) *Proc. Nat. Acad. Sci. USA* 98: 10079-10084.
Silk et al. (1989) *Plant Physiol.* 90: 708-713.
Sugimoto et al. (2001) *Protoplasma* 215: 172-183.
Taylor et al. (2000a) *Plant J.* 24: 305-316
Taylor et al. (2000) *Plant Cell* 12: 2529-2539.
Taylor et al. (1999) *Plant Cell* 11: 769-780.
Treml et al. (2000) *Glycobiology* 10: 493-502.
Trombetta et al. (2001) *Biochemistry* 40: 10717-10722.
Trombetta et al. (1996) *J. Biol. Chem.* 271: 27509-27516.
Vitale (2001) *Plant Cell* 13: 1260-1262
von Schaewen et al. (1993) *Plant Physiol* 102: 1109-1118.
Western et al. (2001) *Plant Physiol* 127: 998-1011.
Western et al. (2000) *Plant Physiol* 122: 345-355.
Williamson et al. (2001 a) *Protoplasma* 215: 116-127.
Williamson et al. (2001) *Cell. Molec. Life Sci.* 58: 1475-1490.
Zuo et al. (2000) *Plant Cell* 12: 1137-1152.

We claim:

1. A method for increasing cellulose biosynthesis in cotton plants, comprising the step of:

providing cells of said cotton plant with a chimeric gene comprising the following operably linked DNA fragments i) a promoter expressible in said cell of said plant;

ii) a DNA region coding for the protein comprising the amino acid sequence of SEQ ID No. 6 or, an amino acid sequence having at least 95% amino acid sequence identity to the amino acid sequence of SEQ ID No 6 and having endo-1,4 β-D-glucanase enzymatic activity;

iii) a 3' region involved in transcription termination and polyadenylation; thereby increasing cellulose biosynthesis in said plant.

2. The method of claim 1, wherein said DNA region comprises the nucleotide sequence of SEQ ID No. 2 from the nucleotide at position 47 to the nucleotide at position 1906.

3. The method of claim 1, wherein said promoter is a constitutive promoter.

4. The method of claim 1, wherein said promoter is a fiber-specific promoter.

5. The method of claim 1, wherein said promoter is an expansin promoter.

6. The method of claim 1, wherein said cellulose biosynthesis is increased in lint fibers.

7. A chimeric gene comprising the following operably linked DNA fragments:

i) a promoter expressible in plant cells;

ii) a DNA region coding for a protein comprising the amino acid sequence of SEQ ID No. 6 or an amino acid sequence having at least 95% amino acid sequence identity to the amino acid sequence of SEQ ID No 6 and having endo-1,4 β-D-glucanase enzymatic activity; and iii) a 3' end region involved in transcription termination and polyadenylation.

8. The chimeric gene of claim 7, wherein said DNA region comprises the nucleotide sequence of SEQ ID No. 2.

9. The chimeric gene of claim 7, wherein said promoter is a constitutive promoter.

10. The chimeric gene of claim 7, wherein said promoter is a fiber-specific promoter.

11. The chimeric gene of claim 7, wherein said promoter is an expansin promoter.

12. A plant cell comprising the chimeric gene of claim 7.

13. A plant comprising the plant cell according to claim 12.

14. A transgenic seed comprising the chimeric gene of claim 1.

* * * * *

SEQUENCE LISTING

```
<160> NUMBER OF SEQ ID NOS: 23

<210> SEQ ID NO 1
<211> LENGTH: 2303
<212> TYPE: DNA
<213> ORGANISM: Arabidopsis thaliana
<220> FEATURE:
<221> NAME/KEY: misc_feature
<222> LOCATION: (121)..(1986)
<223> OTHER INFORMATION: coding RSW2

<400> SEQUENCE: 1

acatttcttc acttccacac acttttactt ctttctctct tctcttctct tctccagatc     60

tgatcccaaa cctttgattc attgttgttg ttctctgctg ctttatcaga gagcatcatc    120

atgtacggaa gagatccatg gggaggtcca ttggagataa acactgcaga ttccgccacc    180

gacgatgatc gtagtcggaa tttaaacgat ttggatcgtg cggctctttc acgtccacta    240

gatgagacgc agcagagttg gttacttggt ccaacggagc agaagaagaa gaagtacgtc    300

gatctcggtt gtattatcgt tagccgcaag atcttcgtct ggactgttgg tactcttgtt    360

gccgccgcgt tactcgccgg attcattacc ttgatcgtta aaactgtgcc gcgtcatcat    420

cctaagactc cgccgccgga taattatact atagctctac acaaagctct taagttcttc    480

aatgctcaga aatctgggaa attgccaaag cataataacg tgtcatggag aggtaattct    540

gggcttcaag atgggaaagg tgaaacagga agcttctata aagatttggt gggaggttat    600

tatgatgctg gtgatgctat caagttcaat ttccccatgg cttatgctat gactatgttg    660

agctggagtg ttattgaata tagtgctaaa tacgaagctg ctggtgagct cactcatgtt    720

aaggagctta tcaaatgggg aactgattac tttctcaaga ctttcaatag tactgctgat    780

tccattgatg atcttgtgtc acaggttgga tcagggaata ctgatgatgg aaatacagat    840

cctaatgacc attactgttg gatgcgacct gaggatatgg actataaaag gcccgtgact    900

acttgtaatg gtggatgttc ggatctcgct gcagagatgg cagctgctct ggcttcagca    960
```

-continued

```
tctattgtat tcaaggataa caaggaatat tctaaaaagc ttgtccatgg tgctaaggtg   1020

gtgtatcagt ttggaaggac gaggagaggg agatatagtg caggcactgc ggaatctagc   1080

aagttctata attcaagtat gtattgggat gagttcattt ggggtggtgc ttggatgtat   1140

tatgctaccg gaaatgtaac gtatctcaat ctaatcaccc aacctactat ggccaagcat   1200

gctggtgcct tctggggtgg cccttactat ggtgtattta gctgggacaa caagcttgct   1260

ggtgctcagt tgctgttgag ccggttgagg ttgtttctga gtcctggata tccatatgaa   1320

gaaattctaa ggaccttcca caatcagacc agcatagtca tgtgctcata cttgcctatt   1380

ttcaacaaat ttaacagaac caatggaggt ttaatagagt tgaatcatgg agctccacag   1440

ccgctgcaat attctgtaaa tgcagctttc ttagcgactc tatacagtga ttatctggat   1500

gctgctgata ctcctggatg gtactgtgga cctaatttct attcgacaag tgtgctacgt   1560

gactttgcta gatcccagat tgattatata ctgggtaaaa accctcggaa aatgagttat   1620

gtcgttggtt ttggcacaaa atacccaaga catgtgcatc acagaggagc ttcgataccc   1680

aagaacaaag tcaagtataa ctgcaaagga ggatggaaat ggagagacag caagaaacca   1740

aacccaaaca cgattgaagg agccatggtt gctggtcctg acaagcgcga cgggtaccgt   1800

gatgtccgta tgaactacaa ctacactgaa ccgactcttg caggcaatgc tggtctagtc   1860

gcagctcttg tggcattatc gggtgaagaa gaagccaccg gtaagataga caaaaacact   1920

attttctcag ctgttcctcc tttgttccct actccaccac ctccaccagc accatggaaa   1980

ccttgagaaa gctagacttg tgtgattctg tcgctgctgc caaaaaaaat gaatgaggta   2040

agaaggattt gggtgtgaga ccagaagatt agaagctaaa cacaagtcag ccataaccaa   2100

actactaagg atttcatttg gctttactag atacaaacac ggggtgggtt actttaccac   2160

aagcattgtc tttcttttct ttttttgggt tgctgttttg ttcttgtgag atatcatata   2220

tatctatgcg ttttactctg tatatgtttg ataccaaact tgtattcttt gataaacaat   2280

ttaatgaact gtattaaact ttt                                           2303
```

<210> SEQ ID NO 2
<211> LENGTH: 2031
<212> TYPE: DNA
<213> ORGANISM: Artificial Sequence
<220> FEATURE:
<223> OTHER INFORMATION: cDNA RSW2 homologue from cotton
<220> FEATURE:
<221> NAME/KEY: misc_feature
<222> LOCATION: (47)..(1906)
<223> OTHER INFORMATION: coding region RSW2 homologue

<400> SEQUENCE: 2

```
ggcacgagcc tgcattttcc gcccactact cttccaaatc ctcatcatgt acggcagaga     60

tccgtgggga ggtcccctgg agataaacgc cactgattct gccactgacg acgacaggag    120

caggaatctg caggacctgg atagggctgc actctctcgc cccttggacg agactcagca    180

aagctggctg cttggccccg gggagcaaaa gaagaagaag aagtacgttg atctcggatg    240

tatcattgtg agccgcaaga tctttgtatg gaccgtgggg accctgctag tctccgccct    300

cctggccgga ctcatcaccc tcatcgtcaa gactgtccca cgtcatcacc accgccactc    360

tccgcccgat aactacactc tggctcttca caaggcgctc atgttcttta atgctcagcg    420

ttctggaaag ctgcccaagc ataataatgt gtcgtggaga gggaactcgg gcctccaaga    480

tggcaaatcc gatccctccg ttttgatgaa agatctggtc ggcggatatt acgatgctgg    540
```

-continued

```
agatgctatc aagtttaact ttcctgcatc tttttcaatg actatgttga gctggagtgt    600
catcgaatac agtgctaaat acgaggctgc cggcgagctc aatcatgtta aagagatcat    660
caaatggggt actgattatc ttctgaagac cttcaacaat actgctgata ccattgacag    720
gattgctgcg caggtaggga taggagatac atctggagga agttcagccc caaatgatca    780
ttattgctgg atgcgccctg aggacattga ttaccccgt  cctgtatatg aatgtcatag    840
ttgctccgat cttgctgctg aaatggctgc tgctttggct tctgcttcca tcgttttcaa    900
agacaacaaa gcatactctc aaaagcttgt ccatggtgcc cgaacactct ttatgtttgc    960
tagggatcaa agaggcagat atagtgctgg tggttctgac cctgccctct tttataattc   1020
ctcaagttac tgggatgagt ttgtttgggg tggagcctgg ttatactatg ccactgggaa   1080
ttcatcctat cttcagttag ctactcatcc taaacttgcc aagcatgctg gtgctttctg   1140
gggtggccca gattatggtg ttcttagctg ggataataag cttgctggtg ctcaggtgct   1200
tctgagccga ttgagattgt ttttgagtcc tgggtatcca tatgaggaaa tattgagtac   1260
gtttcataat caaaccagca taattatgtg ctcattcctt ccggttttca ctagctttaa   1320
tagaacaaaa ggaggtttga ttcagttaaa ccatggaagg cctcagccac tgcaatacgt   1380
agtcaatgca gccttcttag ccgccctata tagtgattat cttgatactg ctgatacacc   1440
tggatggtat tgtggtccca atttctattc aactgatgtc ctgcgtgaat ttgccaaaac   1500
ccagattgat tatatccttg gcaaaaatcc tcgaaaaatg agctatgttg tgggctttgg   1560
taaccattat ccaaagcatg ttcaccatag aggggcatct atccctaaga ataagatcaa   1620
atataactgt aaagggggat ggaaatggag ggatacgtca aaaccaaacc ccaacacact   1680
tgtgggagcc atggtagctg gacctgacaa gcatgatggg tttcgtgatg ttcgcaccaa   1740
ctacaactat acggagccaa ctctagcagg caacgcaggg ttggttgctg cactcgtggc   1800
attgtctggt gacaaggcaa ccgtgattga caagaatacc atttttctg  cagttccacc   1860
aatgtttcct acaccaccac cacctccggc accttggaaa ccatgaaaac gttttgatct   1920
ttcttctgtc catgtgtgac ttacagtctg atgattttgg aattagtttt tggtacgtaa   1980
atgaccttgg aagtgtaagt aacgcaaaag gcaagacagg agatgagtga t            2031
```

<210> SEQ ID NO 3
<211> LENGTH: 4500
<212> TYPE: DNA
<213> ORGANISM: Arabidopsis thaliana

<400> SEQUENCE: 3

```
gtgtactgcg agaactgctt attacataca tggcagataa tccgcgtaga agaagggttt     60
aacggagacg aatttgaact ctccgacgaa ataatcgtct tctccggcat catcttcaga    120
aagctattcc aaattagggt tttgactttt gattgaagaa gacaggtcta gaaacttaca    180
tacaccaatt ttaaaatcga gtttgggccg aattatggac cgtactttgg gctatgggcc    240
ttcattttaa taaacaggtc ggatatatcc accggacccg gaatgatcgt cttcctcagt    300
gttgtatttt ggctttcctc attgcttcct caatctaagg atttccatga acaaggaact    360
aaaatgagat ctcttctctt tgtactatca ctcatttgct tttgctctca aacagcactt    420
tcatggaaga aggaagagtt tcgcagctgt gaccaaactc cattttgtaa acgcgctcga    480
tctcgtactc ccggcgcgtg ttctctaatt gtcggcgatg tttccatcac tgatggagat    540
ctcgtagcga agcttctacc gaaagcgcct aatcaaggcg atggggatca gatcaagccg    600
ttgattcttt ctctctcagt ttacaaggat gggatcgtgc ggcttaaaat cgatgaggac    660
```

-continued

```
cattcgttga acccgccgaa gaagaggttc caagttcctg atgtggtagt gtctgagttt     720
gaggagaaga agatctggct gcagaaagta gcgacggaga cgatctctgg agacactagt     780
ccgtcttcag tagtttatgt atccgatggt tacgaggcgg tggtgcgaca cgatccgttt     840
gaggtgtatg tgcgtgagaa atcaggtgat cgccgtcgcg ttgtgtcatt gaattctcat     900
ggattatttg attttgagca gttggggagg aaaactgaag gagataactg ggaagagaaa     960
tttaggactc atacagattc tagaccatct ggtcctcaat ctattagttt cgatgtttcg    1020
ttttatgatt ccagtttcgt ttatggaatt cctgaacacg ccactagctt cgcgttgaag    1080
cctaccaagg gtcctggagt tgaggaatct gaaccctaca ggctttttaa tctagatgtg    1140
tttgaatacg atcatgaatc accgtttggg ctttacgggt cgattccgtt catggtttcg    1200
catgggaagt ctggtaaaac ttcaggattt ttctggttga atgctgcgga aatgcagatt    1260
gatgtgttgg ctaatggttg ggatgcagag agtggtattt ctttgccttc tagtcacagt    1320
aggatcgaca cattctggat gagcgaggca gggattgtgg atacattctt tttcgttggg    1380
cctgagccaa aggatgttgt aaagcagtat gcaagtgtga caggtacttc agccatgcct    1440
cagttgtttg ccactggtta tcatcaatgt aggtggaact acaaagatga ggaggatgtg    1500
gcacaggtgg actcgaaatt cgatgaacac gatattcctt atgatgttct ctggcttgac    1560
attgagcata cagatgggaa gagatacttt acatgggata gtgtgttgtt tcctcatcca    1620
gaggagatgc aaaagaaatt ggctgcaaag ggtaggaaga tggtgaccat tgtggatcct    1680
catatcaaga gggatgactc atacttctta cacaaagagg ctactcagat gggatactat    1740
gttaaggatt catctggaaa agactttgat ggttggtgct ggcctggttc atcatcttac    1800
attgatatgt tgagcccaga gattagaaaa tggtggggtg ggaggttctc gtataagaac    1860
tatgttggtt caactccatc attgtacacc tggaatgaca tgaatgagcc ttctgtattc    1920
aatggtcccg aggtataact ttctgtctga atggtctttt tttcttgttc cgttattgtt    1980
tttctgtaat ctgtatagct catttctcat attcattttg ggattgcagt tgaatatagc    2040
aatccattgt tttctattg cacaattatg gatatgtttg aactctgata gattatacat     2100
cccttatctt gcatactatg acacctttta ttaattattg cactactaaa gcaagtattt    2160
taagatccat tttatgttta tgtggtttta cattggatat ttgtttctgt gacttcttta    2220
agagtggagt gtaagctatg gttgcatatc tccacctctg atttgcttat atcgtagaaa    2280
gtttatcata tatgtaaagg tctattactg agatgaagac tggcactttt ttctttcttt    2340
tttgttggag taggttacta tgccaagaga tgcattacat gttgggggtg ttgaacacag    2400
agaagttcat aacgcatatg gatattactt ccacatggcg acttccgatg gacttgttat    2460
gcgtgaagaa ggaaaggata ggccttttgt attgtcaaga gcaatctttc ccggcactca    2520
aagatacgga gcaatttgga ctggagataa cacagccgaa tgggaacacc ttagagtctc    2580
cattccaatg atattgacac ttggtcttac tggaattaca ttctctggta caaacaaatt    2640
tagctgttca aattctgctg gcgttttttt tttctttctc aaatttaatg gaagttttct    2700
tttcttttgc aggagctgat attggtgggt tttttggaaa tcctgaacca gaacttctag    2760
ttaggtggta ccaagtgggt gcttactatc catttttcag ggggtcatgct catcacgata   2820
ccaaaagacg agagccttgg ttgtttgggt aagatgtgat ttagtactta attttttctt    2880
gtcaagaggt attattttag tatgcggtcc aggtctagtc tatggatatt tgcttgatgg    2940
atgatcaagc agattgaaat gtagtgatac tggttattga gaaaagaata caattgcgga    3000
```

-continued

```
aactaaaacc tggtgttgca ctctagtcag ttgattgtct aaatagttag gccattagtt   3060

tcatcaagta ggcattgcaa cggttgtcca gaagtctctc tgcctttgtt ttgctggctc   3120

ataaatgttg cactttctca ttcgaatcaa atcaatgttc tcttgtttca gtgaacggaa   3180

cacagaactc atgagagatg ccatacacac tcgttacaca ctgctcccat acttctacac   3240

gttgttcaga gaagcaaacg ttacgggtgt tcctgttgta cgcccattat ggatggaatt   3300

cccgcaagat gaagctactt ttagcaacga tgaagccttc atggtcggta gtggtctact   3360

ggttcaagga gtttacacca aggtacttga gcgctaagta caacttccta cttatttata   3420

ttttggcctt tgtatctctt tacttaatca tatactccag ataaatgatc aaaccctgcc   3480

acataccctc ttctcgtctt tctgcaaaat tagggaacaa cgcaagcttc cgtgtatttg   3540

cctggcaaag aatcatggta tgacttgaga aacggtaaga cttacgttgg aggcaagact   3600

cacaagatgg atgctccaga ggagagtatt cctgcgtttc aaaaggcagg aaccatcatc   3660

ccaaggaagg accggtttag gcgaagttcc tctcaaatgg acaatgatcc ttatactttg   3720

gtacgtacaa cacttgcatc acactgtttt atcatctgct atcagcacca tgaacaaagt   3780

aaaaccggtt ggtaaaaaga ttatctctga aagtgaaatc ccaatgataa actatgtgat   3840

ctaacatcta aaacccttca ggtggtagct ttgaacagtt ctcaagaagc agaaggtgaa   3900

ctctacatcg atgacggcaa aagctttgaa ttcagacgag gctcttacat ccatcgtcgc   3960

ttcgtcttct caaagggtgt tcttacatca acgaacttag ctcctccaga agctcgtctc   4020

tcttcccaat gcttgatcga cagaattatc ctcttgggac acagctcagg tccaaaatct   4080

gcgttggtgg aaccgttgaa tcaaaaggca gagattgaga tgggacctct gcgaatgggt   4140

gggcttgtag cttcctcggg tacaaaggtg ttgactatcc gcaaaccggg tgttcgagtg   4200

gaccaagact ggaccgtaaa gattctgtga ttgaacggtt tgaaccagtt tcactcatgg   4260

ccgttagagt ggccgaaatc tgcttttccg gcgacggaat atcacacttt ttaatatatg   4320

tttggagatt tagacttaaa tagttgtaag agctaacagt ttgaaagtca ctttgcattg   4380

ttgtttatct tcatataaat gagtttagat tttgataatt tcagaattcg tggaatcata   4440

attaacaatt ttgataggga aaaataattt gttttttta gtcagagggt caaataatct   4500
```

```
<210> SEQ ID NO 4
<211> LENGTH: 1773
<212> TYPE: DNA
<213> ORGANISM: Artificial Sequence
<220> FEATURE:
<223> OTHER INFORMATION: cDNA RSW3 homologue from cotton (partial 3'
      end)
<220> FEATURE:
<221> NAME/KEY: misc_feature
<222> LOCATION: (2)..(1576)
<223> OTHER INFORMATION: C-terminal part of the coding region

<400> SEQUENCE: 4

atatgatgtt ttgtggcttg atattgagca tactgatgga aagaggtatt tcacatggga     60

taagatgcta ttcccacatc cagaagagat gcaaaggaaa ttggctgcca aaggtaggca    120

tatggtgaca attgtggatc cgcatattaa gagggatgag tcatttcact tgcacaagga    180

tgcttcccag agggggtatt atgtaaagga tgcaactggc aaggattatg atgggtggtg    240

ctggccaggc tcctcctcct acccagatat gttaaatccc gagattaggt catggtgggc    300

tgagaagttc tcctatgata attatgtcgg ttcaactcct tcattgtaca tttggaatga    360

catgaatgag ccttctgtgt ttaatggacc tgaggtgaca atgcccagag atgctttaca    420
```

```
tgttggtgga gtggaacatc gggagttaca taatgcctat ggatattact tccacatggc    480

aacagctgaa ggccttctaa agcgtggaga tggtaaggac agaccttttg tcttgtccag    540

agcattcttt gctggaagtc aaaggtatgg agcagtctgg actggtgata attcggcaga    600

ttgggatcat ctcagggttt cagtcccaat ggttttgacg cttggtctta ctggaatgac    660

attctctggg gctgatgttg gtggattttt tggcaatcct gagcctgagt tattagtgcg    720

ttggtatcaa cttggtgctt attatccttt ctttagaggt catgctcatc atgacacaaa    780

aagacgagag ccttggttgt ttggtgaacg aaataccgca cttatgagag atgccatacg    840

aattcgttac accttgcttc catacttcta cacattattc agagaagcaa atgttagtgg    900

tgttcctgtt gtacggccat tatggatgga gttcccatct gatgaagcag ctttcagcaa    960

tgatgaagcc ttcatggttg ggaacagtct tttagtacaa gggatctata ctgcaagggc   1020

taaacatgca tcagtatatt tgcctgggaa ggaatcgtgg tacgacctta gaacaggaac   1080

tgcatataag ggaggaaagg tccataaact tgaagtttca gaagagagca ttcctgcttt   1140

ccaaagagct ggcacaatag tgccaagaaa agaccggttc cgtagaagct ccacacaaat   1200

ggtgcatgat ccttacacac tggtaatagc tctgaacagt tcccaagcag ctgaaggtga   1260

actctatgtt gatgatggaa aaagctatga cttcaaacat ggggcataca tccatcgccg   1320

ctttgtgttc tcgaatgggc atctaacatc ctctcccgtt ggcaactcta ggttttcgtc   1380

tgactgcatt atcgagcggg ttattcttct tggatttacc cctggggcta aaactgctct   1440

tgtcgaacca ggaaatcaga aggctgaaat cgaacttggt ccacttcggt tcgggggaca   1500

acatgctgct gttgctgtaa ccatccggaa gcctggtgtg agggtggctg aagattggaa   1560

gataaaaatt ttgtaggatg tctatttagt tcggtgaaaa tgtaatgcca agtaaagctc   1620

tcctgctact tcgttattct cgacttttta gagtttatga tggagaaaac tggaaagccg   1680

ttgacatttc cttcgttcaa tttactttct acttttaaga atttaaaaaa aaagtcgacg   1740

cggccgcgaa ttccggaccg gtacctgcag gcg                                1773
```

<210> SEQ ID NO 5
<211> LENGTH: 621
<212> TYPE: PRT
<213> ORGANISM: Arabidopsis thaliana

<400> SEQUENCE: 5

```
Met Tyr Gly Arg Asp Pro Trp Gly Gly Pro Leu Glu Ile Asn Thr Ala
1               5                   10                  15

Asp Ser Ala Thr Asp Asp Asp Arg Ser Arg Asn Leu Asn Asp Leu Asp
            20                  25                  30

Arg Ala Ala Leu Ser Arg Pro Leu Asp Glu Thr Gln Gln Ser Trp Leu
        35                  40                  45

Leu Gly Pro Thr Glu Gln Lys Lys Lys Lys Tyr Val Asp Leu Gly Cys
    50                  55                  60

Ile Ile Val Ser Arg Lys Ile Phe Val Trp Thr Val Gly Thr Leu Val
65                  70                  75                  80

Ala Ala Ala Leu Leu Ala Gly Phe Ile Thr Leu Ile Val Lys Thr Val
                85                  90                  95

Pro Arg His His Pro Lys Thr Pro Pro Pro Asp Asn Tyr Thr Ile Ala
            100                 105                 110

Leu His Lys Ala Leu Lys Phe Phe Asn Ala Gln Lys Ser Gly Lys Leu
        115                 120                 125

Pro Lys His Asn Asn Val Ser Trp Arg Gly Asn Ser Gly Leu Gln Asp
```

```
    130                 135                 140

Gly Lys Gly Glu Thr Gly Ser Phe Tyr Lys Asp Leu Val Gly Gly Tyr
145                 150                 155                 160

Tyr Asp Ala Gly Asp Ala Ile Lys Phe Asn Phe Pro Met Ala Tyr Ala
                165                 170                 175

Met Thr Met Leu Ser Trp Ser Val Ile Glu Tyr Ser Ala Lys Tyr Glu
            180                 185                 190

Ala Ala Gly Glu Leu Thr His Val Lys Glu Leu Ile Lys Trp Gly Thr
        195                 200                 205

Asp Tyr Phe Leu Lys Thr Phe Asn Ser Thr Ala Asp Ser Ile Asp Asp
    210                 215                 220

Leu Val Ser Gln Val Gly Ser Gly Asn Thr Asp Asp Gly Asn Thr Asp
225                 230                 235                 240

Pro Asn Asp His Tyr Cys Trp Met Arg Pro Glu Asp Met Asp Tyr Lys
                245                 250                 255

Arg Pro Val Thr Thr Cys Asn Gly Gly Cys Ser Asp Leu Ala Ala Glu
            260                 265                 270

Met Ala Ala Ala Leu Ala Ser Ala Ser Ile Val Phe Lys Asp Asn Lys
        275                 280                 285

Glu Tyr Ser Lys Lys Leu Val His Gly Ala Lys Val Val Tyr Gln Phe
    290                 295                 300

Gly Arg Thr Arg Arg Gly Arg Tyr Ser Ala Gly Thr Ala Glu Ser Ser
305                 310                 315                 320

Lys Phe Tyr Asn Ser Ser Met Tyr Trp Asp Glu Phe Ile Trp Gly Gly
                325                 330                 335

Ala Trp Met Tyr Tyr Ala Thr Gly Asn Val Thr Tyr Leu Asn Leu Ile
            340                 345                 350

Thr Gln Pro Thr Met Ala Lys His Ala Gly Ala Phe Trp Gly Gly Pro
        355                 360                 365

Tyr Tyr Gly Val Phe Ser Trp Asp Asn Lys Leu Ala Gly Ala Gln Leu
    370                 375                 380

Leu Leu Ser Arg Leu Arg Leu Phe Leu Ser Pro Gly Tyr Pro Tyr Glu
385                 390                 395                 400

Glu Ile Leu Arg Thr Phe His Asn Gln Thr Ser Ile Val Met Cys Ser
                405                 410                 415

Tyr Leu Pro Ile Phe Asn Lys Phe Asn Arg Thr Asn Gly Gly Leu Ile
            420                 425                 430

Glu Leu Asn His Gly Ala Pro Gln Pro Leu Gln Tyr Ser Val Asn Ala
        435                 440                 445

Ala Phe Leu Ala Thr Leu Tyr Ser Asp Tyr Leu Asp Ala Ala Asp Thr
    450                 455                 460

Pro Gly Trp Tyr Cys Gly Pro Asn Phe Tyr Ser Thr Ser Val Leu Arg
465                 470                 475                 480

Asp Phe Ala Arg Ser Gln Ile Asp Tyr Ile Leu Gly Lys Asn Pro Arg
                485                 490                 495

Lys Met Ser Tyr Val Val Gly Phe Gly Thr Lys Tyr Pro Arg His Val
            500                 505                 510

His His Arg Gly Ala Ser Ile Pro Lys Asn Lys Val Lys Tyr Asn Cys
        515                 520                 525

Lys Gly Gly Trp Lys Trp Arg Asp Ser Lys Lys Pro Asn Pro Asn Thr
    530                 535                 540

Ile Glu Gly Ala Met Val Ala Gly Pro Asp Lys Arg Asp Gly Tyr Arg
545                 550                 555                 560
```

-continued

```
Asp Val Arg Met Asn Tyr Asn Tyr Thr Glu Pro Thr Leu Ala Gly Asn
                565                 570                 575

Ala Gly Leu Val Ala Ala Leu Val Ala Leu Ser Gly Glu Glu Glu Ala
            580                 585                 590

Thr Gly Lys Ile Asp Lys Asn Thr Ile Phe Ser Ala Val Pro Pro Leu
        595                 600                 605

Phe Pro Thr Pro Pro Pro Pro Pro Ala Pro Trp Lys Pro
    610                 615                 620


<210> SEQ ID NO 6
<211> LENGTH: 619
<212> TYPE: PRT
<213> ORGANISM: cotton

<400> SEQUENCE: 6

Met Tyr Gly Arg Asp Pro Trp Gly Gly Pro Leu Glu Ile Asn Ala Thr
1               5                   10                  15

Asp Ser Ala Thr Asp Asp Asp Arg Ser Arg Asn Leu Gln Asp Leu Asp
            20                  25                  30

Arg Ala Ala Leu Ser Arg Pro Leu Asp Glu Thr Gln Gln Ser Trp Leu
        35                  40                  45

Leu Gly Pro Gly Glu Gln Lys Lys Lys Lys Lys Tyr Val Asp Leu Gly
    50                  55                  60

Cys Ile Ile Val Ser Arg Lys Ile Phe Val Trp Thr Val Gly Thr Leu
65                  70                  75                  80

Leu Val Ser Ala Leu Leu Ala Gly Leu Ile Thr Leu Ile Val Lys Thr
                85                  90                  95

Val Pro Arg His His His Arg His Ser Pro Pro Asp Asn Tyr Thr Leu
            100                 105                 110

Ala Leu His Lys Ala Leu Met Phe Phe Asn Ala Gln Arg Ser Gly Lys
        115                 120                 125

Leu Pro Lys His Asn Asn Val Ser Trp Arg Gly Asn Ser Gly Leu Gln
    130                 135                 140

Asp Gly Lys Ser Asp Pro Ser Val Leu Met Lys Asp Leu Val Gly Gly
145                 150                 155                 160

Tyr Tyr Asp Ala Gly Asp Ala Ile Lys Phe Asn Phe Pro Ala Ser Phe
                165                 170                 175

Ser Met Thr Met Leu Ser Trp Ser Val Ile Glu Tyr Ser Ala Lys Tyr
            180                 185                 190

Glu Ala Ala Gly Glu Leu Asn His Val Lys Glu Ile Ile Lys Trp Gly
        195                 200                 205

Thr Asp Tyr Leu Leu Lys Thr Phe Asn Asn Thr Ala Asp Thr Ile Asp
    210                 215                 220

Arg Ile Ala Ala Gln Val Gly Ile Gly Asp Thr Ser Gly Gly Ser Ser
225                 230                 235                 240

Ala Pro Asn Asp His Tyr Cys Trp Met Arg Pro Glu Asp Ile Asp Tyr
                245                 250                 255

Pro Arg Pro Val Tyr Glu Cys His Ser Cys Ser Asp Leu Ala Ala Glu
            260                 265                 270

Met Ala Ala Ala Leu Ala Ser Ala Ser Ile Val Phe Lys Asp Asn Lys
        275                 280                 285

Ala Tyr Ser Gln Lys Leu Val His Gly Ala Arg Thr Leu Phe Met Phe
    290                 295                 300

Ala Arg Asp Gln Arg Gly Arg Tyr Ser Ala Gly Gly Ser Asp Pro Ala
```

-continued

```
305                 310                 315                 320

Leu Phe Tyr Asn Ser Ser Ser Tyr Trp Asp Glu Phe Val Trp Gly Gly
                325                 330                 335

Ala Trp Leu Tyr Tyr Ala Thr Gly Asn Ser Ser Tyr Leu Gln Leu Ala
            340                 345                 350

Thr His Pro Lys Leu Ala Lys His Ala Gly Ala Phe Trp Gly Gly Pro
        355                 360                 365

Asp Tyr Gly Val Leu Ser Trp Asp Asn Lys Leu Ala Gly Ala Gln Val
    370                 375                 380

Leu Leu Ser Arg Leu Arg Leu Phe Leu Ser Pro Gly Tyr Pro Tyr Glu
385                 390                 395                 400

Glu Ile Leu Ser Thr Phe His Asn Gln Thr Ser Ile Ile Met Cys Ser
                405                 410                 415

Phe Leu Pro Val Phe Thr Ser Phe Asn Arg Thr Lys Gly Gly Leu Ile
            420                 425                 430

Gln Leu Asn His Gly Arg Pro Gln Pro Leu Gln Tyr Val Val Asn Ala
        435                 440                 445

Ala Phe Leu Ala Ala Leu Tyr Ser Asp Tyr Leu Asp Thr Ala Asp Thr
    450                 455                 460

Pro Gly Trp Tyr Cys Gly Pro Asn Phe Tyr Ser Thr Asp Val Leu Arg
465                 470                 475                 480

Glu Phe Ala Lys Thr Gln Ile Asp Tyr Ile Leu Gly Lys Asn Pro Arg
                485                 490                 495

Lys Met Ser Tyr Val Val Gly Phe Gly Asn His Tyr Pro Lys His Val
            500                 505                 510

His His Arg Gly Ala Ser Ile Pro Lys Asn Lys Ile Lys Tyr Asn Cys
        515                 520                 525

Lys Gly Gly Trp Lys Trp Arg Asp Thr Ser Lys Pro Asn Pro Asn Thr
    530                 535                 540

Leu Val Gly Ala Met Val Ala Gly Pro Asp Lys His Asp Gly Phe Arg
545                 550                 555                 560

Asp Val Arg Thr Asn Tyr Asn Tyr Thr Glu Pro Thr Leu Ala Gly Asn
                565                 570                 575

Ala Gly Leu Val Ala Ala Leu Val Ala Leu Ser Gly Asp Lys Ala Thr
            580                 585                 590

Val Ile Asp Lys Asn Thr Ile Phe Ser Ala Val Pro Pro Met Phe Pro
        595                 600                 605

Thr Pro Pro Pro Pro Pro Ala Pro Trp Lys Pro
    610                 615


<210> SEQ ID NO 7
<211> LENGTH: 921
<212> TYPE: PRT
<213> ORGANISM: Arabidopsis thaliana

<400> SEQUENCE: 7

Met Arg Ser Leu Leu Phe Val Leu Ser Leu Ile Cys Phe Cys Ser Gln
1               5                   10                  15

Thr Ala Leu Ser Trp Lys Lys Glu Glu Phe Arg Ser Cys Asp Gln Thr
            20                  25                  30

Pro Phe Cys Lys Arg Ala Arg Ser Arg Thr Pro Gly Ala Cys Ser Leu
        35                  40                  45

Ile Val Gly Asp Val Ser Ile Thr Asp Gly Asp Leu Val Ala Lys Leu
    50                  55                  60
```

-continued

```
Leu Pro Lys Ala Pro Asn Gln Gly Asp Gly Asp Gln Ile Lys Pro Leu
65                  70                  75                  80

Ile Leu Ser Leu Ser Val Tyr Lys Asp Gly Ile Val Arg Leu Lys Ile
                85                  90                  95

Asp Glu Asp His Ser Leu Asn Pro Pro Lys Lys Arg Phe Gln Val Pro
            100                 105                 110

Asp Val Val Val Ser Glu Phe Glu Glu Lys Lys Ile Trp Leu Gln Lys
        115                 120                 125

Val Ala Thr Glu Thr Ile Ser Gly Asp Thr Ser Pro Ser Ser Val Val
    130                 135                 140

Tyr Val Ser Asp Gly Tyr Glu Ala Val Val Arg His Asp Pro Phe Glu
145                 150                 155                 160

Val Tyr Val Arg Glu Lys Ser Gly Asp Arg Arg Arg Val Val Ser Leu
                165                 170                 175

Asn Ser His Gly Leu Phe Asp Phe Glu Gln Leu Gly Arg Lys Thr Glu
            180                 185                 190

Gly Asp Asn Trp Glu Glu Lys Phe Arg Thr His Thr Asp Ser Arg Pro
        195                 200                 205

Ser Gly Pro Gln Ser Ile Ser Phe Asp Val Ser Phe Tyr Asp Ser Ser
    210                 215                 220

Phe Val Tyr Gly Ile Pro Glu His Ala Thr Ser Phe Ala Leu Lys Pro
225                 230                 235                 240

Thr Lys Gly Pro Gly Val Glu Glu Ser Glu Pro Tyr Arg Leu Phe Asn
                245                 250                 255

Leu Asp Val Phe Glu Tyr Asp His Glu Ser Pro Phe Gly Leu Tyr Gly
            260                 265                 270

Ser Ile Pro Phe Met Val Ser His Gly Lys Ser Gly Lys Thr Ser Gly
        275                 280                 285

Phe Phe Trp Leu Asn Ala Ala Glu Met Gln Ile Asp Val Leu Ala Asn
    290                 295                 300

Gly Trp Asp Ala Glu Ser Gly Ile Ser Leu Pro Ser Ser His Ser Arg
305                 310                 315                 320

Ile Asp Thr Phe Trp Met Ser Glu Ala Gly Ile Val Asp Thr Phe Phe
                325                 330                 335

Phe Val Gly Pro Glu Pro Lys Asp Val Val Lys Gln Tyr Ala Ser Val
            340                 345                 350

Thr Gly Thr Ser Ala Met Pro Gln Leu Phe Ala Thr Gly Tyr His Gln
        355                 360                 365

Cys Arg Trp Asn Tyr Lys Asp Glu Glu Asp Val Ala Gln Val Asp Ser
    370                 375                 380

Lys Phe Asp Glu His Asp Ile Pro Tyr Asp Val Leu Trp Leu Asp Ile
385                 390                 395                 400

Glu His Thr Asp Gly Lys Arg Tyr Phe Thr Trp Asp Ser Val Leu Phe
                405                 410                 415

Pro His Pro Glu Glu Met Gln Lys Lys Leu Ala Ala Lys Gly Arg Lys
            420                 425                 430

Met Val Thr Ile Val Asp Pro His Ile Lys Arg Asp Asp Ser Tyr Phe
        435                 440                 445

Leu His Lys Glu Ala Thr Gln Met Gly Tyr Tyr Val Lys Asp Ser Ser
    450                 455                 460

Gly Lys Asp Phe Asp Gly Trp Cys Trp Pro Gly Ser Ser Ser Tyr Ile
465                 470                 475                 480

Asp Met Leu Ser Pro Glu Ile Arg Lys Trp Trp Gly Gly Arg Phe Ser
```

-continued

```
                485                 490                 495

Tyr Lys Asn Tyr Val Gly Ser Thr Pro Ser Leu Tyr Thr Trp Asn Asp
            500                 505                 510

Met Asn Glu Pro Ser Val Phe Asn Gly Pro Glu Val Thr Met Pro Arg
        515                 520                 525

Asp Ala Leu His Val Gly Gly Val Glu His Arg Glu Val His Asn Ala
    530                 535                 540

Tyr Gly Tyr Tyr Phe His Met Ala Thr Ser Asp Gly Leu Val Met Arg
545                 550                 555                 560

Glu Glu Gly Lys Asp Arg Pro Phe Val Leu Ser Arg Ala Ile Phe Pro
                565                 570                 575

Gly Thr Gln Arg Tyr Gly Ala Ile Trp Thr Gly Asp Asn Thr Ala Glu
            580                 585                 590

Trp Glu His Leu Arg Val Ser Ile Pro Met Ile Leu Thr Leu Gly Leu
        595                 600                 605

Thr Gly Ile Thr Phe Ser Gly Ala Asp Ile Gly Gly Phe Phe Gly Asn
    610                 615                 620

Pro Glu Pro Glu Leu Leu Val Arg Trp Tyr Gln Val Gly Ala Tyr Tyr
625                 630                 635                 640

Pro Phe Phe Arg Gly His Ala His His Asp Thr Lys Arg Arg Glu Pro
                645                 650                 655

Trp Leu Phe Gly Glu Arg Asn Thr Glu Leu Met Arg Asp Ala Ile His
            660                 665                 670

Thr Arg Tyr Thr Leu Leu Pro Tyr Phe Tyr Thr Leu Phe Arg Glu Ala
        675                 680                 685

Asn Val Thr Gly Val Pro Val Val Arg Pro Leu Trp Met Glu Phe Pro
    690                 695                 700

Gln Asp Glu Ala Thr Phe Ser Asn Asp Glu Ala Phe Met Val Gly Ser
705                 710                 715                 720

Gly Leu Leu Val Gln Gly Val Tyr Thr Lys Gly Thr Thr Gln Ala Ser
                725                 730                 735

Val Tyr Leu Pro Gly Lys Glu Ser Trp Tyr Asp Leu Arg Asn Gly Lys
            740                 745                 750

Thr Tyr Val Gly Gly Lys Thr His Lys Met Asp Ala Pro Glu Glu Ser
        755                 760                 765

Ile Pro Ala Phe Gln Lys Ala Gly Thr Ile Ile Pro Arg Lys Asp Arg
    770                 775                 780

Phe Arg Arg Ser Ser Ser Gln Met Asp Asn Asp Pro Tyr Thr Leu Val
785                 790                 795                 800

Val Ala Leu Asn Ser Ser Gln Glu Ala Glu Gly Glu Leu Tyr Ile Asp
                805                 810                 815

Asp Gly Lys Ser Phe Glu Phe Arg Arg Gly Ser Tyr Ile His Arg Arg
            820                 825                 830

Phe Val Phe Ser Lys Gly Val Leu Thr Ser Thr Asn Leu Ala Pro Pro
        835                 840                 845

Glu Ala Arg Leu Ser Ser Gln Cys Leu Ile Asp Arg Ile Ile Leu Leu
    850                 855                 860

Gly His Ser Ser Gly Pro Lys Ser Ala Leu Val Glu Pro Leu Asn Gln
865                 870                 875                 880

Lys Ala Glu Ile Glu Met Gly Pro Leu Arg Met Gly Gly Leu Val Ala
                885                 890                 895

Ser Ser Gly Thr Lys Val Leu Thr Ile Arg Lys Pro Gly Val Arg Val
            900                 905                 910
```

-continued

Asp Gln Asp Trp Thr Val Lys Ile Leu
915 920

<210> SEQ ID NO 8
<211> LENGTH: 524
<212> TYPE: PRT
<213> ORGANISM: cotton

<400> SEQUENCE: 8

Tyr Asp Val Leu Trp Leu Asp Ile Glu His Thr Asp Gly Lys Arg Tyr
1 5 10 15

Phe Thr Trp Asp Lys Met Leu Phe Pro His Pro Glu Glu Met Gln Arg
20 25 30

Lys Leu Ala Ala Lys Gly Arg His Met Val Thr Ile Val Asp Pro His
35 40 45

Ile Lys Arg Asp Glu Ser Phe His Leu His Lys Asp Ala Ser Gln Arg
50 55 60

Gly Tyr Tyr Val Lys Asp Ala Thr Gly Lys Asp Tyr Asp Gly Trp Cys
65 70 75 80

Trp Pro Gly Ser Ser Ser Tyr Pro Asp Met Leu Asn Pro Glu Ile Arg
85 90 95

Ser Trp Trp Ala Glu Lys Phe Ser Tyr Asp Asn Tyr Val Gly Ser Thr
100 105 110

Pro Ser Leu Tyr Ile Trp Asn Asp Met Asn Glu Pro Ser Val Phe Asn
115 120 125

Gly Pro Glu Val Thr Met Pro Arg Asp Ala Leu His Val Gly Gly Val
130 135 140

Glu His Arg Glu Leu His Asn Ala Tyr Gly Tyr Tyr Phe His Met Ala
145 150 155 160

Thr Ala Glu Gly Leu Leu Lys Arg Gly Asp Gly Lys Asp Arg Pro Phe
165 170 175

Val Leu Ser Arg Ala Phe Phe Ala Gly Ser Gln Arg Tyr Gly Ala Val
180 185 190

Trp Thr Gly Asp Asn Ser Ala Asp Trp Asp His Leu Arg Val Ser Val
195 200 205

Pro Met Val Leu Thr Leu Gly Leu Thr Gly Met Thr Phe Ser Gly Ala
210 215 220

Asp Val Gly Gly Phe Phe Gly Asn Pro Glu Pro Glu Leu Leu Val Arg
225 230 235 240

Trp Tyr Gln Leu Gly Ala Tyr Tyr Pro Phe Phe Arg Gly His Ala His
245 250 255

His Asp Thr Lys Arg Arg Glu Pro Trp Leu Phe Gly Glu Arg Asn Thr
260 265 270

Ala Leu Met Arg Asp Ala Ile Arg Ile Arg Tyr Thr Leu Leu Pro Tyr
275 280 285

Phe Tyr Thr Leu Phe Arg Glu Ala Asn Val Ser Gly Val Pro Val Val
290 295 300

Arg Pro Leu Trp Met Glu Phe Pro Ser Asp Glu Ala Ala Phe Ser Asn
305 310 315 320

Asp Glu Ala Phe Met Val Gly Asn Ser Leu Leu Val Gln Gly Ile Tyr
325 330 335

Thr Ala Arg Ala Lys His Ala Ser Val Tyr Leu Pro Gly Lys Glu Ser
340 345 350

Trp Tyr Asp Leu Arg Thr Gly Thr Ala Tyr Lys Gly Gly Lys Val His

-continued

```
        355                 360                 365

Lys Leu Glu Val Ser Glu Glu Ser Ile Pro Ala Phe Gln Arg Ala Gly
    370                 375                 380

Thr Ile Val Pro Arg Lys Asp Arg Phe Arg Arg Ser Ser Thr Gln Met
385                 390                 395                 400

Val His Asp Pro Tyr Thr Leu Val Ile Ala Leu Asn Ser Ser Gln Ala
                405                 410                 415

Ala Glu Gly Glu Leu Tyr Val Asp Asp Gly Lys Ser Tyr Asp Phe Lys
            420                 425                 430

His Gly Ala Tyr Ile His Arg Arg Phe Val Phe Ser Asn Gly His Leu
        435                 440                 445

Thr Ser Ser Pro Val Gly Asn Ser Arg Phe Ser Ser Asp Cys Ile Ile
    450                 455                 460

Glu Arg Val Ile Leu Leu Gly Phe Thr Pro Gly Ala Lys Thr Ala Leu
465                 470                 475                 480

Val Glu Pro Gly Asn Gln Lys Ala Glu Ile Glu Leu Gly Pro Leu Arg
                485                 490                 495

Phe Gly Gly Gln His Ala Ala Val Ala Val Thr Ile Arg Lys Pro Gly
            500                 505                 510

Val Arg Val Ala Glu Asp Trp Lys Ile Lys Ile Leu
        515                 520
```

<210> SEQ ID NO 9
<211> LENGTH: 2766
<212> TYPE: DNA
<213> ORGANISM: Arabidopsis thaliana

<400> SEQUENCE: 9

```
atgagatctc ttctctttgt actatcactc atttgctttt gctctcaaac agcactttca      60

tggaagaagg aagagtttcg cagctgtgac caaactccat tttgtaaacg cgctcgatct     120

cgtactcccg gcgcgtgttc tctaattgtc ggcgatgttt ccatcactga tggagatctc     180

gtagcgaagc ttctaccgaa agcgcctaat caaggcgatg gggatcagat caagccgttg     240

attctttctc tctcagttta caaggatggg atcgtgcggc ttaaaatcga tgaggaccat     300

tcgttgaacc cgccgaagaa gaggttccaa gttcctgatg tggtagtgtc tgagtttgag     360

gagaagaaga tctggctgca gaaagtagcg acggagacga tctctggaga cactagtccg     420

tcttcagtag tttatgtatc cgatggttac gaggcggtgg tgcgacacga tccgtttgag     480

gtgtatgtgc gtgagaaatc aggtgatcgc cgtcgcgttg tgtcattgaa ttctcatgga     540

ttatttgatt ttgagcagtt ggggaggaaa actgaaggag ataactggga agagaaattt     600

aggactcata cagattctag accatctggt cctcaatcta ttagtttcga tgtttcgttt     660

tatgattcca gtttcgttta tggaattcct gaacacgcca ctagcttcgc gttgaagcct     720

accaagggtc ctggagttga ggaatctgaa ccctacaggc tttttaatct agatgtgttt     780

gaatacgatc atgaatcacc gtttgggctt tacgggtcga ttccgttcat ggtttcgcat     840

gggaagtctg gtaaaacttc aggatttttc tggttgaatg ctgcggaaat gcagattgat     900

gtgttggcta atggttggga tgcagagagt ggtatttctt tgccttctag tcacagtagg     960

atcgacacat tctggatgag cgaggcaggg attgtggata cattcttttt cgttgggcct    1020

gagccaaagg atgttgtaaa gcagtatgca agtgtgacag gtacttcagc catgcctcag    1080

ttgtttgcca ctggttatca tcaatgtagg tggaactaca aagatgagga ggatgtggca    1140

caggtggact cgaaattcga tgaacacgat attccttatg atgttctctg gcttgacatt    1200
```

-continued

```
gagcatacag atgggaagag atactttaca tgggatagtg tgttgtttcc tcatccagag   1260
gagatgcaaa agaaattggc tgcaaagggt aggaagatgg tgaccattgt ggatcctcat   1320
atcaagaggg atgactcata cttcttacac aaagaggcta ctcagatggg atactatgtt   1380
aaggattcat ctggaaaaga ctttgatggt tggtgctggc ctggttcatc atcttacatt   1440
gatatgttga gcccagagat tagaaaatgg tggggtggga ggttctcgta taagaactat   1500
gttggttcaa ctccatcatt gtacacctgg aatgacatga atgagccttc tgtattcaat   1560
ggtcccgagg ttactatgcc aagagatgca ttacatgttg gggtgttga acacagagaa    1620
gttcataacg catatggata ttacttccac atggcgactt ccgatggact tgttatgcgt   1680
gaagaaggaa aggataggcc ttttgtattg tcaagagcaa tctttcccgg cactcaaaga   1740
tacggagcaa tttggactgg agataacaca gccgaatggg aacaccttag agtctccatt   1800
ccaatgatat tgacacttgg tcttactgga attacattct ctggagctga tattggtggg   1860
ttttttggaa atcctgaacc agaacttcta gttaggtggt accaagtggg tgcttactat   1920
ccatttttca ggggtcatgc tcatcacgat accaaaagac gagagccttg gttgtttggt   1980
gaacggaaca cagaactcat gagagatgcc atacacactc gttacacact gctcccatac   2040
ttctacacgt tgttcagaga agcaaacgtt acgggtgttc ctgttgtacg cccattatgg   2100
atggaattcc cgcaagatga agctactttt agcaacgatg aagccttcat ggtcggtagt   2160
ggtctactgg ttcaaggagt ttacaccaag ggaacaacgc aagcttccgt gtatttgcct   2220
ggcaaagaat catggtatga cttgagaaac ggtaagactt acgttggagg caagactcac   2280
aagatggatg ctccagagga gagtattcct gcgtttcaaa aggcaggaac catcatccca   2340
aggaaggacc ggtttaggcg aagttcctct caaatggaca atgatcctta tactttggtg   2400
gtagctttga acagttctca agaagcagaa ggtgaactct acatcgatga cggcaaaagc   2460
tttgaattca gacgaggctc ttacatccat cgtcgcttcg tcttctcaaa gggtgttctt   2520
acatcaacga acttagctcc tccagaagct cgtctctctt cccaatgctt gatcgacaga   2580
attatcctct tgggacacag ctcaggtcca aaatctgcgt tggtggaacc gttgaatcaa   2640
aaggcagaga ttgagatggg acctctgcga atgggtgggc ttgtagcttc ctcgggtaca   2700
aaggtgttga ctatccgcaa accgggtgtt cgagtggacc aagactggac cgtaaagatt   2760
ctgtga                                                              2766
```

<210> SEQ ID NO 10
<211> LENGTH: 29
<212> TYPE: DNA
<213> ORGANISM: Artificial sequence
<220> FEATURE:
<223> OTHER INFORMATION: oligonucleotide PCR primer

<400> SEQUENCE: 10

```
ccgctcgagc gggcatttc cgcccacta                                        29
```

<210> SEQ ID NO 11
<211> LENGTH: 29
<212> TYPE: DNA
<213> ORGANISM: Artificial Sequence
<220> FEATURE:
<223> OTHER INFORMATION: oligonucleotide PCR primer

<400> SEQUENCE: 11

```
cgggatcccg tcacacatgg acagaagaa                                       29
```

```
<210> SEQ ID NO 12
<211> LENGTH: 19
<212> TYPE: DNA
<213> ORGANISM: Artificial Sequence
<220> FEATURE:
<223> OTHER INFORMATION: oligonucleotide PCR primer

<400> SEQUENCE: 12

gacggcgtct agaagattc                                                    19


<210> SEQ ID NO 13
<211> LENGTH: 19
<212> TYPE: DNA
<213> ORGANISM: Artificial Sequence
<220> FEATURE:
<223> OTHER INFORMATION: oligonucleotide PCR primer

<400> SEQUENCE: 13

taacttatcg ggcttctgc                                                    19


<210> SEQ ID NO 14
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 14

ccctcgcttg gtacaaggta t                                                 21


<210> SEQ ID NO 15
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 15

tcctgatcct ctcaccacgt a                                                 21


<210> SEQ ID NO 16
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 16

cgtagtggtc tactggttca a                                                 21


<210> SEQ ID NO 17
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 17

tgagctgtgt cccaagagga t                                                 21


<210> SEQ ID NO 18
<211> LENGTH: 21
<212> TYPE: DNA
<213> ORGANISM: Artificial Sequence
<220> FEATURE:
<223> OTHER INFORMATION: oligonucleotide PCR primer
```

<400> SEQUENCE: 18
ggtgatgagg ataccagcga t 21

<210> SEQ ID NO 19
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 19
cccactccct aaccggagtt t 21

<210> SEQ ID NO 20
<211> LENGTH: 35
<212> TYPE: DNA
<213> ORGANISM: Artificial Sequence
<220> FEATURE:
<223> OTHER INFORMATION: oligonucleotide PCR primer

<400> SEQUENCE: 20
ccgctcgagc ggtttcactc acaactgtgg tctct 35

<210> SEQ ID NO 21
<211> LENGTH: 34
<212> TYPE: DNA
<213> ORGANISM: Artificial Sequence
<220> FEATURE:
<223> OTHER INFORMATION: oligonucleotide PCR primer

<400> SEQUENCE: 21
ccgctcgagc ggtctcctaa gtcctaaccc cata 34

<210> SEQ ID NO 22
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 22
cgggatgaag aggatgtaga g 21

<210> SEQ ID NO 23
<211> LENGTH: 21
<212> TYPE: DNA
<213> ORGANISM: Artificial Sequence
<220> FEATURE:
<223> OTHER INFORMATION: oligonucleotide PCR primer

<400> SEQUENCE: 23
gaacccctga gatgatccca a 21